US010060905B2

(12) United States Patent
Magniette

(10) Patent No.: US 10,060,905 B2
(45) Date of Patent: Aug. 28, 2018

(54) LIQUID MEDIUM AND SAMPLE VIAL FOR USE IN A METHOD FOR DETECTING CANCEROUS CELLS IN A CELL SAMPLE

(71) Applicant: OVIZIO IMAGING SYSTEMS NV/SA, Brussels (BE)

(72) Inventor: Olivier Magniette, Deurle (BE)

(73) Assignee: OVIZIO IMAGING SYSTEMS NV/SA, Brussels (BE)

( * ) Notice: Subject to any disclaimer, the term of this patent is extended or adjusted under 35 U.S.C. 154(b) by 0 days.

(21) Appl. No.: 14/359,553

(22) PCT Filed: Nov. 20, 2012

(86) PCT No.: PCT/EP2012/073124
§ 371 (c)(1),
(2) Date: May 20, 2014

(87) PCT Pub. No.: WO2013/076089
PCT Pub. Date: May 30, 2013

(65) Prior Publication Data
US 2014/0329231 A1 Nov. 6, 2014

(30) Foreign Application Priority Data

Nov. 21, 2011 (EP) .................................. 11189986

(51) Int. Cl.
| | | |
|---|---|---|
| *C12Q 1/68* | (2018.01) | |
| *G01N 33/574* | (2006.01) | |
| *C12P 19/34* | (2006.01) | |
| *A61K 38/00* | (2006.01) | |
| *C07K 16/30* | (2006.01) | |
| *G01N 33/487* | (2006.01) | |
| *B01L 3/00* | (2006.01) | |
| *G01N 21/03* | (2006.01) | |
| *A61B 10/02* | (2006.01) | |
| *G01N 1/40* | (2006.01) | |
| *G03H 1/00* | (2006.01) | |
| *G03H 1/04* | (2006.01) | |

(52) U.S. Cl.
CPC ... *G01N 33/48778* (2013.01); *A61B 10/0291* (2013.01); *B01L 3/502* (2013.01); *B01L 3/5082* (2013.01); *G01N 1/405* (2013.01); *G01N 21/03* (2013.01); *G01N 33/57411* (2013.01); *A61B 2010/0216* (2013.01); *B01L 2200/0647* (2013.01); *B01L 2200/0652* (2013.01); *B01L 2300/023* (2013.01); *B01L 2300/042* (2013.01); *B01L 2300/0609* (2013.01); *B01L 2300/0681* (2013.01); *B01L 2300/0803* (2013.01); *B01L 2300/0832* (2013.01); *B01L 2300/0851* (2013.01); *B01L 2300/0858* (2013.01); *B01L 2400/086* (2013.01); *G03H 1/0443* (2013.01); *G03H 2001/005* (2013.01)

(58) Field of Classification Search
CPC .... A61K 31/11; A61K 2300/00; A61K 45/06; G01N 33/57407; C12Q 1/6886
See application file for complete search history.

(56) References Cited

U.S. PATENT DOCUMENTS

| | | |
|---|---|---|
| 4,786,594 A | 11/1988 | Khanna et al. |
| 5,089,416 A | 2/1992 | Schwartz |
| 5,243,409 A | 9/1993 | Sagner |
| 5,256,571 A | 10/1993 | Hurley et al. |
| 5,495,333 A | 2/1996 | Konda |
| 6,249,345 B1 | 6/2001 | Kraack |
| 6,327,377 B1 | 12/2001 | Rutenberg |
| 6,361,934 B1 | 3/2002 | Acton |
| 6,394,966 B1 | 5/2002 | Gill |
| 6,651,008 B1 | 11/2003 | Vaisberg et al. |
| 6,809,862 B2 | 10/2004 | Behnsen et al. |
| 6,924,094 B1 | 8/2005 | Gingeras et al. |
| 6,954,667 B2 | 10/2005 | Treado |
| 7,009,700 B2 | 3/2006 | Dubois et al. |

(Continued)

FOREIGN PATENT DOCUMENTS

| | | |
|---|---|---|
| CN | 202 808 799 | 3/2013 |
| EP | 0479231 A1 | 4/1992 |

(Continued)

OTHER PUBLICATIONS

Beitsch et al., "Detection of carcinoma cells in the blodd of breast cancer patients", 2000, The American Journal of Surgery, 180:446-449.*
Beitsch et al., "Detection of carcinoma cells in the blood of breast cancer patients", The American Journal of Surgery, 2000, 180:446-449).*
Boulet et al., Cancer Epidemiology, Biomarkers & Prevention, 2008, 17(4):810-817.*
Sahasrabuddhe et al., Future Microbiol., 2011 6(9):1-25.*
Beitsch et al., 2000, The American Journal of Surgery, 180(6):446-449.*
Beitsch et al., "Detection of carcinoma cells in the blood of breast cancer patients," *The American Journal of Surgery*, vol. 180, pp. 446-449 (Dec. 2000).

(Continued)

*Primary Examiner* — Barry A Chestnut
(74) *Attorney, Agent, or Firm* — Knobbe, Martens, Olson & Bear, LLP

(57) ABSTRACT

The current invention concerns a method for determining the presence of a (pre)cancerous cell in a liquid cell sample, comprising the steps of: —suspending and preserving a cell sample obtained from a subject in a sample vial comprising a liquid medium, said liquid medium comprises means for labeling cells or epitope(s) on or in said cells; —obtaining data from said labelled liquid cell sample; and —determining the presence of said (pre)cancerous cells based on said obtained data; characterized in that said data comprises morphological data and biomarker data. In a further aspect, the invention relates to a liquid medium for fixing, preserving and labeling cells in a cell sample and a sample vial specifically designed to be used in conjunction with the current method.

11 Claims, 12 Drawing Sheets

(56) References Cited

U.S. PATENT DOCUMENTS

| | | |
|---|---|---|
| 7,286,222 B2 | 10/2007 | Gardner |
| 7,616,320 B2 | 11/2009 | Javidi et al. |
| 8,599,383 B2* | 12/2013 | Teitell ............... G01J 3/453 356/341 |
| 9,569,664 B2 | 2/2017 | Judkewitz |
| 9,675,974 B2 | 6/2017 | Jooris et al. |
| 9,684,281 B2 | 6/2017 | Mathius et al. |
| 9,846,151 B2 | 12/2017 | Magniette |
| 9,904,248 B2 | 2/2018 | Mathuis et al. |
| 2002/0064328 A1 | 5/2002 | Neuberger |
| 2002/0106119 A1 | 8/2002 | Foran |
| 2002/0164063 A1 | 11/2002 | Heckman |
| 2003/0113832 A1 | 6/2003 | Lauf |
| 2003/0199649 A1 | 10/2003 | Orbison et al. |
| 2005/0036181 A1 | 2/2005 | Marquet et al. |
| 2005/0272103 A1 | 12/2005 | Chen |
| 2006/0014239 A1 | 1/2006 | Luttmann et al. |
| 2006/0088814 A1 | 4/2006 | Hecht et al. |
| 2006/0132799 A1 | 6/2006 | Franck et al. |
| 2006/0283945 A1 | 12/2006 | Excoffier |
| 2007/0216906 A1 | 9/2007 | Javidi et al. |
| 2008/0018966 A1 | 1/2008 | Dubois et al. |
| 2008/0032325 A1 | 2/2008 | DiMarzio |
| 2008/0113340 A1* | 5/2008 | Schlegel ............. C12Q 1/6886 435/5 |
| 2008/0137933 A1 | 6/2008 | Kim |
| 2008/0242556 A1 | 10/2008 | Cao et al. |
| 2008/0317325 A1 | 12/2008 | Ortyn et al. |
| 2009/0082637 A1 | 3/2009 | Galperin |
| 2009/0092227 A1 | 4/2009 | David |
| 2009/0244667 A1 | 10/2009 | Frentz |
| 2009/0296083 A1 | 12/2009 | Saski et al. |
| 2009/0305393 A1 | 12/2009 | Joeris |
| 2010/0034442 A1 | 2/2010 | Minakuchi |
| 2010/0196871 A1 | 8/2010 | Dodgson |
| 2010/0315501 A1 | 12/2010 | Ludwig |
| 2011/0134426 A1 | 6/2011 | Kaduchak |
| 2011/0204256 A1 | 8/2011 | Patt |
| 2011/0212440 A1 | 9/2011 | Viovy |
| 2012/0015391 A1 | 1/2012 | Zhang et al. |
| 2012/0200901 A1 | 8/2012 | Dubois |
| 2012/0218379 A1 | 8/2012 | Ozcan |
| 2014/0038171 A1 | 2/2014 | Metzger et al. |
| 2014/0049634 A1 | 2/2014 | Tafas |
| 2014/0139625 A1 | 5/2014 | Mathuis et al. |
| 2014/0193850 A1 | 7/2014 | Jooris et al. |
| 2014/0195568 A1 | 7/2014 | Mathuis et al. |
| 2014/0349336 A1 | 11/2014 | Magniette |
| 2015/0056607 A1 | 2/2015 | Jooris et al. |
| 2015/0248109 A1 | 9/2015 | Mathuis et al. |
| 2016/0184817 A1 | 6/2016 | Jooris et al. |
| 2017/0023472 A1 | 1/2017 | Pavillion et al. |
| 2017/0205222 A1 | 7/2017 | Mathius et al. |
| 2017/0261930 A1 | 9/2017 | Mathuis et al. |

FOREIGN PATENT DOCUMENTS

| | | |
|---|---|---|
| EP | 1524491 A1 | 4/2005 |
| EP | 2008715 A1 | 12/2008 |
| WO | WO 98/57152 | 12/1998 |
| WO | WO 99/44593 A1 | 9/1999 |
| WO | WO 2004/057464 A2 | 7/2004 |
| WO | WO 2004/102111 A1 | 11/2004 |
| WO | WO 2006/047252 A1 | 5/2006 |
| WO | WO 2007/073345 A1 | 6/2007 |
| WO | WO 2009/051741 A2 | 4/2009 |
| WO | WO 2009/154558 A1 | 12/2009 |
| WO | WO2009151632 | * 12/2009 |
| WO | WO2009154558 | * 12/2009 |
| WO | WO 2011/042442 A1 | 4/2011 |
| WO | WO 2011/068764 A2 | 6/2011 |
| WO | WO 2011/099925 A1 | 8/2011 |
| WO | WO2011099925 | * 8/2011 |
| WO | WO 2011/154143 A1 | 12/2011 |
| WO | WO 2013/120886 A1 | 8/2013 |
| WO | WO 2014/044823 A1 | 3/2014 |

OTHER PUBLICATIONS

Kemper et al., "Monitoring of laser micro manipulated optically trapped cells by digital holographic microscopy," *J Biophoton*, vol. 3(7), pp. 425-431 (2010).

Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).

Weigum et al., "Nano-Bio-Chip Sensor Platform for Examination of Oral Exfoliative Cytology," *Cancer Prevention Research*, vol. 3, pp. 518-528 (2010).

White et al., "Isolation of Stool-Derived Mucus Provides a High Yield of Colonocytes Suitable for Early Detection of Colorectal Carcinoma," *Cancer Epidemiol Biomarkers Prev*, vol. 8, pp. 2006-2013 (2009).

Fook Chiong Cheong et al., "Flow visualization and flow cytometry with holographic video microscopy", Proceedings of the SPIE—The International Society for Optical Engineering SPIE—The International Society for Optical Engineering USA, vol. 7619, 2010, XP040518833, ISSN: 0277-786X. Published Feb. 10, 2010.

Frank Dubois et al., "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.

Mihailescu et al., "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.

Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar 18, 2009).

Daneshpanah et al., "3D Holographic Imaging and Trapping for Non-Invasive Cell Identification and Tracking," Journal of Display Technology, vol. 6(10), pp. 490-499 (Oct. 2010).

Extended European Search Report for European Patent Application No. 16151897.2, dated Jul. 21, 2016.0.

Fook Chiong Cheong et al. "Flow visualization and flow cytometry with holographic video microscopy", Proceedings of the SPIE—The International Society for Optical Engineering SPIE—The International Society for Optical Engineering USA, vol. 7619, 2010, XP040518833, ISSN: 0277-786X. Published Feb. 10, 2010.

Frank Dubois et al. "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.

Fu et al., "Quantitative DIC microscopy using an off-axis self-interference approach," Optics Letters, vol. 35(14), pp. 2370-2372 (Jul. 15, 2010).

Indebetouw, G. et al. Feb. 20, 2007. Scanning holographic microscopy with resolution exceeding the Rayleigh limit of the objective by superposition of off-axis holograms. Applied Optics 46(6): 993-1000. speif. pp. 993, 994.

Kemper, B. et al. Feb. 1, 2008. Digital holographic microscopy for live cell applications and technical inspection. Applied Optics 47(4): A52-A61. specif. pp. A52, 53, 56, 59.

Kemper et al., "Investigation of living pancreas tumor cells by digital holographic microscopy," Journal of Biomedical Optics, vol. 11(3), pp. 034005-1-034005-8 (May/Jun. 2006).

Kemper et al., "Simplified approach for quantitative digital holographic phase contrast imaging of living cells," Journal of Biomedical Optics, vol. 16(2), pp. 026014-1-026014-4 (Feb. 2011).

(56) References Cited

OTHER PUBLICATIONS

Kemper et al., "Self interference digital holographic microscopy approach for inspection of technical and biological phase specimens," Proceedings of the SPIE—The International Society for Optical Engineering SPIE—The International Society for Optical Engineering USA, vol. 8082, May 23, 2011.
Lee et al., "Incremental feature weight learning and its application to a shape-based query system," Pattern Recognition Letters, vol. 23, pp. 865-874 (2002).
Marin et al., "A meta-index for querying distributed moving object database servers," Information Systems, vol. 35, pp. 637-661 (2010).
McClatchey et al., "Object Databases in a Distributed Scientific Workflow Application," Information Technology, 1997, BIWIT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.
Mihailescu M et al., "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.
Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).
Nenadic et al., "A Possibility of Applying Differential Digital Holography in Manufacturing Process," 48th International Symposium ELMAR-2006, Jun. 7-9, 2006, Zadar, Croatia, pp. 103-106.
Sun et al., "Visualization of fast-moving cells in vivo using digital holographic video microscopy," Journal of Biomedical Optics, vol. 13(1), pp. 014007-1-014007-9 (Jan./Feb. 2008).
Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).
Yong-Seok Choi et al., "Lateral and cross-lateral focusing of spherical particles in a square microchannel", Lab on a Chip, vol. 11, No. 3, pp. 460-465, XP55032064, ISSN: 1473-0197, DOI: 10.1039/c0lc00212g. Published Feb. 1, 2011.
Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.

International Search Report for Application No. PCT/EP2014/066312, dated Jan. 10, 2014, in 3 pages.
Kosmeier et al., "Determination of the Integral Refractive Index of Cells in Suspension by Digital Holographic Phase Contrast Microscopy", Biophotonics: Photonic Solutions for Better Health Care, Proc. of SPIE vol. 6991, 699110 (2008).
Ling et al., "Application of Flow Cytometry for Biomarker-Based Cervical Cancer Cells Detection," Diagnostic Cytopathology, vol. 36, No. 2, dated 2008.
Wang et al., "Nanoscale Nuclear Architecture for Cancer Diagnosis Beyond Pathology Via Spatial-Domain Low-Coherence Quantitative Phase Microscopy," Journal of Biomedical Optics , vol. 15(6), 066028, published Dec. 23, 2010.
Wikipedia, "Quantitative Phase-Contrast Microscopy" retrieved from http://en.wikipedia.org/w/index.php?title=Quantitative_phase-contrast_microscopy&oldid= 734365574, last modified on Aug. 13, 2016.
Yeom et al., "Automatic Identification of Biological Microorganisms Using Three-Dimensional Complex Morphology," Journal of Biomedical Optics, vol. 11(2), 0124017, published Mar. 24, 2006.
Kosmeier et al., "Determination of the Integral Refractive Index of Cells in Suspension by Digital Holographic Phase Contrast Microscopy", Biophotonics: Photonic Solutions for Better Health Care, Proc. of SPIE col. 6991, 699110, (2008).
Ling et al., "Application of Flow Cytometry for Biomarker-Based Cervical Cancer Cells Detection," Diagnostic Cytopathology, vol. 36, No. 2, dated 2008.
Mann et al., "Dual Modality Live Cell Imaging with Multiple-Wavelength Digital Holography and Epi-Fluorescence," Topical Editor: Dr. Tristan Colomb, 3D Res.2, Accepted: Nov. 3, 2010.
Pavillon, et al., "Cell Morphology and Intracellular ionic homeostasis explored with a multimodal approach combining epifluorescene and digital holographic microscopy," Journal of Biophotonics, vol. No. 7, pp. 432-436, Accepted. Mar. 5, 2010.
Pin Wang et al., "Nanoscale Nuclear Architecture for Cancer Diagnosis beyond Pathology Via Spatial-Domain Low-Coherence Qualitative Phase Microscopy," Journal of Biomedical Optics , vol. 15(6), 066028, dated Nov./Dec. 2010.
Wikipedia "Quantitative Phase-Contrast Microscopy" retreieved from http://en.wikipedia.org/w/index.php?title=Quantitative_phase-contrast_microscopy&oldid= 734365574, last modified on Aug. 13, 2016.
Yeom, "Automatic Identification of Biological Microorganisms using Three-Dimensional Complex Morphology," Journal of Biomedical Optics, vol. 11(2), 0124017, dated Mar./Apr. 2006.

* cited by examiner

A

B

C

A

B

LIQUID MEDIUM AND SAMPLE VIAL FOR USE IN A METHOD FOR DETECTING CANCEROUS CELLS IN A CELL SAMPLE

CROSS-REFERENCE TO RELATED APPLICATIONS

This application is the U.S. National Phase under 35 U.S.C. § 371 of International Application PCT/EP2012/073124, filed Nov. 20, 2012, which claims priority to EP 11189986.0, filed Nov. 21, 2011.

TECHNICAL FIELD

The invention pertains to the technical field of the early diagnosis of carcinomas as well as their preliminary stages, particularly carcinomas of the cervix and uterus.

BACKGROUND

To diagnose whether a patient is suffering from cancer or has a predisposition, cells need to be sampled from a patient and a thorough analysis of the cell sample is required in order to evaluate whether abnormal or aberrant cells are present. Mainly, a pathologist or other skilled medical personnel will base the diagnosis on specific characteristics of the cells in the sample, such as cell morphology, the presence of certain types of cells or proteins and more. These cytological tests are based on a two-dimensional presentation of the cells present in the sample and mostly require the fixation of cells on a substratum and the use of dyes or stainings to visualize specific features of the cells. This is a time consuming and cumbersome work, and requires well-trained specialists. Moreover, as many of the solutions used to fix and stain the cells, this approach will inevitably lead to loss of cell structures and information stored therein. This might thus interfere with the possibility of a reliable interpretation and diagnosis from the sample. Inadequate processing of a sample may lead to an increased number of false negatives diagnoses. For instance, of the over 50 million cervical cytological PAP smears, which are performed in the USA each year, a high false-negative interpretation rate of 20-40% has been described (Williams et al., 1998), frequently leading to fatal consequences. Most of these false negatives are the result of inadequate sample processing.

Since 1990 many advanced technologies focusing on sampling, smear preparation, or screening quality control have been developed and introduced into the practical work to prevent the false negative rate in screening. These commercial devices can be divided into the following categories based on their approaches: (1) for a better slide preparation to reduce sampling error, such as thin-layered liquid based preparation (ThinPrep™, SurePath, Tripath); (2) for reducing workload and screening error, such as autoscreening system (ThinPrep Imaging System, Cytyc, Boxborough, Mass.) and FocalPoint System (Tripath Imaging, Burlington, N.C.); (3) for laboratory quality control, such as rescreening (Papnet); and (4) for quality assurance, such as proficiency test. However, most of these devices are not designed to assist diagnosis by supplying the calculable parameters to eliminate interpretation errors and inter-observer discrepancy. In addition, it is not applicable for general cytological laboratory because of high cost and technical or linguistic gaps. Thus, without a reproducible and quantitative tool, it is still an unsolved problem for a routine cytological laboratory to improve the diagnostic divergence caused by visual observation.

The Papanicolaou (PAP) smear has been the cornerstone of cervical cancer screening since 1949. By definition, the PAP smear is a stain performed on cells smeared on a slide and visualized by microscopy. Following the advent of liquid-based cervical cytology (LBC), cells from the cervix were obtained using a brush, suspended in a fixative solution, and then applied to a slide prior to staining. Highly trained cytotechnologists and cytopathologists review the stained slides looking for evidence of abnormal cells based on morphological appearances (as indicated in Table 1).

TABLE 1

| Low grade squamous intraepithelial lesion (LSIL) | High grade squamous intraepithelial lesion (HSIL) |
|---|---|
| Caviation (Mild increase) N/C ratio Hyperchromasia | (Moderate-Marked increase) N/C* Ratio Coarse Chromatin Hyperchromasia Irregular Nuclear Contour Single Abn Cells Syncytial Aggregates Pleomorphism |

*N/C = nuclear to cytoplasmic ratio

Because of the necessity to use slides for the PAP smear, other biomarkers used for cervical cancer screening, especially those used for the molecular detection of HPV DNA, are performed on a separate aliquot of the LBC. Therefore, the throughput is not desirable to accommodate the 60-70 million cervical cytology specimens obtained every year in the US and the 150+ million samples worldwide. Further, molecular techniques performed on a slide are cumbersome and time consuming, characteristics that are not amenable to cervical cancer screening.

Clinically, the PAP smear and HPV testing are used together though they are very disparate technologies. The PAP smear has relatively low sensitivity (50%) and relatively high specificity (90%) for high grade cervical lesions (pre-cervical cancer and cervical cancer). Conversely, HPV DNA testing has high sensitivity (>90%) but low specificity (30%) for high grade cervical lesions (pre-cervical cancer and cervical cancer. These performance characteristics have supported the combined use of these tests for effective cervical cancer screening.

In general, the field of cancer diagnosis is in need for methods and devices that analyses cell samples in a non-destructive, non-detrimental and objective manner. Preferably, a diagnosis is performed on the 'raw' sample whereby information is provided on the status of the sample and the cells present without the need for further processing of the cell sample (e.g. centrifuging, cell lysis, etc.). Advantageously, the diagnosis is based on both morphological data and protein expression profiles of said cells.

The latter will undeniably lead to a more reliable diagnosis method as more accurate information will be obtained from the analyzing sample.

SUMMARY OF THE INVENTION

The current invention provides a method of predicting the presence of cancerous cells in a liquid cell sample obtained from a subject. More in particular, the current invention provides a method according to claim 1. The method allows a fast and accurate prediction, without the need of cumbersome and laborious handling steps. Prediction occurs on the basis of morphological and biomarker data of the raw sample, whereby both data are simultaneously obtained from the raw sample.

The data of the current method may be obtained by any suitable system or application, implementable with the current method. Preferably, said all data is obtained by Digital Holographic Microscopy (DHM). DHM allows retrieving a vast collection of two-dimensional, three-dimensional and fluorescence data related to a sample in a fast and accurate manner.

In a second aspect, the invention discloses a liquid medium as described in claim 12, a sample vial according to claim 17 and a kit according to claim 19. These are specifically developed to allow reliable and correct prediction.

DESCRIPTION OF FIGURES

FIG. 10A depicts the phase-contrast image of the cell, while FIG. 10B shows the three-dimensional image from the same field of cells, obtained by DHM. FIG. 10C is a top-view of the cells, obtained by DHM.

DETAILED DESCRIPTION OF THE INVENTION

Figure 1A:
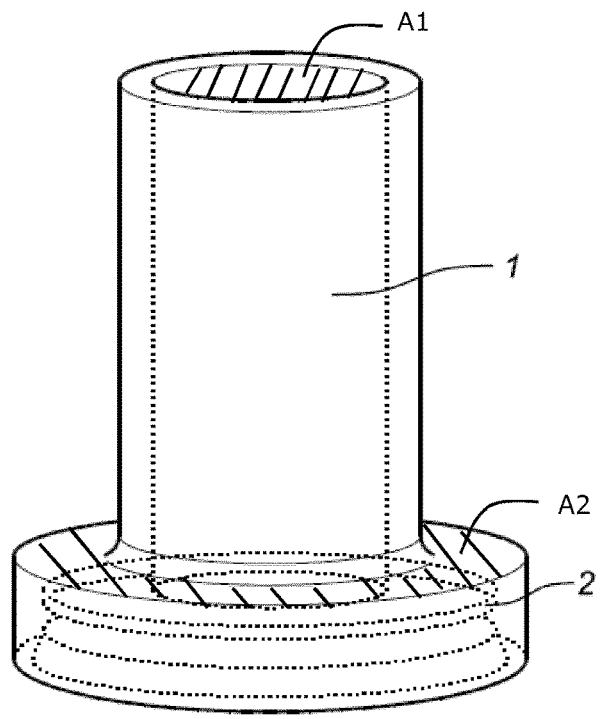
FIGS. 1-7 and 9 depict various embodiments of the sample vial according to the current invention.

The current invention provides methods of predicting whether in a cell sample obtained from a subject, preferably a human subject, cancerous cells are present. Aspects of the methods include obtaining morphological as well as biomarker data and/or non-specific cell data from a cell sample by assaying the sample in suspension, directly after obtainment of the cell sample, without any prior sample handling or processing such as centrifugation, re-suspending, hybridization, etc. Prediction is based on two different types of data in order to eventually come to a very reliable and trustworthy diagnosis. Also provided are consumables specifically developed and optimised to be used in conjunction with the method of the current invention and a system that finds use in practicing the method. The method and system find use in a variety of applications, specifically in the field of the early diagnosis of carcinomas, including cervical cancer screening applications. Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In further describing embodiments of the invention, aspects of embodiments of the methods will be described first in greater detail. Next, embodiments of systems that may be used in practicing methods of the invention are reviewed.

As summarized above, embodiments of the invention are directed to methods of predicting or diagnosing the presence of cancerous or pre-cancerous cells in a sample obtained from a subject. For instance, the presence of a cervical intraepithelial neoplasia (CIN) lesion or cervical cancer may be predicted.

The term "cell sample" or "sample" as used herein refers to any specimen obtained from a subject, preferably a biological organism, preferably a living organism, which comprises cells from said biological organism. The term relates also to specimen obtained from non-living, i.e. dead biological organisms, in particular recently deceased organisms. In preferred embodiments of the present invention a cell sample may be derived from an animal, preferably from a mammal, e.g. from a cat, a dog, a swine, a horse, a cattle, a sheep, a goat, a rabbit, a rat, a mouse, a monkey. Particularly preferred is a sample obtained from a human being.

In one embodiment said cell sample is a tissue sample, a biopsy sample, a blood sample, a serum sample, a brushing or scraping sample from oral cavities, nipple secretions, skin lesions, and eye brushings, a fine-needle-aspiration sample, a smear sample, a mucoid specimens taken from respiratory and gastrointestinal tracts and body fluids such as serous effusions or urinary or cerebrospinal fluids.

In a preferred embodiment, said sample is a smear sample.

In another preferred embodiment, said smear sample is a cervical sample.

The term "CIN lesion" (also referred to in the art as cervical dysplasia) is used in its conventional sense to refer to the abnormal growth of squamous cells on the surface of the cervix. As is known in the art, CIN lesions may be histologically graded as CIN1, CIN2/3, CIN2 and CIN3. CIN1 lesions are those lesions that are confined to the basal ⅓ of the epithelium, and have the least risk of developing into a cancerous lesion, relative to the other categories of lesions. CIN2 lesions are characterized by moderate dysplasia confined to the basal ⅔ of the epithelium. CIN3 lesions (sometimes referred to by those of skill in the art as cervical carcinoma in situ) are categorized by the presence of severe dysplasia that traverses more than ⅔ of the epithelium. The CIN2/3 category (i.e., CIN2+) collectively refers to both CIN2 and CIN3 lesions.

Embodiments of the invention are characterized by predicting the presence of a CIN lesion in a subject with a high degree of sensitivity and specificity. By predicting is meant to prognosticate or foresee the presence of a CIN lesion in the subject without actually taking a biopsy of the cervix of the subject. The terms sensitivity and specificity are used in their conventional sense. As such, sensitivity is a measure of the proportion of actual positives (as opposed to false positives) that are correctly identified while specificity is a measure of negatives which are correctly identified. Embodiments of the invention may predict the presence or absence of any type of cancerous cell in a cell sample obtained from a subject, independent of the origin of the cell sample. More in particular, embodiments may predict the presence of a CIN lesion. Embodiments of the invention may also predict the type of CIN lesion, e.g., whether the CIN lesion is a CIN1, CIN2+, CIN2 or CIN3 lesion. Embodiments of the methods make this prediction, e.g., whether a lesion is present, what type of lesion is present (such as whether a CIN2+ lesion is present) with a high degree of sensitivity and specificity. In some instances, sensitivity is 85% or more, such as 90% or more, including 95% or more. In some instances, specificity is 85% or more, such as 87% or more, including 90% or more.

Aspects of the methods include obtaining both: (1) morphological data and (2) biomarker data from a labelled liquid sample of cells in suspension from the subject. In other words, a sample comprising cells is collected from the subject by any convenient protocol, whereby the sample is solubilised or suspended and preserved in a sample vial comprising a liquid medium. In a preferred embodiment, said liquid medium comprises means for labelling cells or epitope(s) on or in said cells. Preferably, the solubilisation of the obtained sample occurs immediately after obtainment of the sample from said subject. For instance, in the case of a cervical sample, the sample can be obtained from the cervix of a patient by a practitioner using a cell collector such as a swab or cervical brush, after which the practitioner (e.g. the gynecologist) immediately will transfer the collected cells to a sample vial for solubilising and preservation of the sample.

The cells are suspended in a specifically developed liquid medium (e.g., as described in greater detail below), and are assayed to obtain both morphological data and biomarker/ non-specific cell data. Thus, a labelled liquid sample according to aspects of the methods may be a biomarker labelled liquid sample, a non-specific cell labelled liquid sample, or a biomarker and non-specific cell labelled liquid sample. The liquid medium is thus developed for use in the methods and systems according the current invention and assures preservation of mammalian cells in suspension at ambient temperature. The solution enhances maintenance of the nuclear structure of the cells, in that it maintains cell membranes intact. The solution also effectively destroys microbial pathogens in a sample, and inhibits retroviral activity.

The liquid medium of the current invention preferably comprises:
- a fixative;
- a buffering agent which maintains the pH of the liquid medium between 2 and 7;
- an anti-clumping agent for preventing cell aggregates; and
- means for labelling cells or epitope(s) on or in said cells.

Suitable fixatives or fixation reagents are those that fix the cells at a desired timepoint. Any convenient fixation reagent may be employed, where suitable fixation reagents include, but are not limited to: aldehydes such as formaldehyde, paraformaldehyde, glutaraldehyde; zinc-based fixatives such as zinc chloride, zinc sulfate or zinc acetate; alcohols such as methanol, ethanol, isopropanol; acetone; or any combination hereof.

The fixative should be used at an appropriate concentration, depending on the nature of said fixative. For example, paraformaldehyde used at a final concentration of about 1 to 4%, more preferably 1 to 2% has been found to be a good cross-linking fixative.

In one embodiment, said fixative is an alcohol. More preferably, the alcohol is methanol or ethanol or a mixture thereof. Other alcohols which may be used include isopropanol and ethanol among others. This alcohol constituent maintains cell DNA integrity and retains the detail of the cell nucleus for subsequent cytological staining and analysis. In one embodiment of the invention, the alcohol is present in an amount of approximately 45% to 55% by solution. Solutions containing 60% or above of the alcohol constituent tend to exhibit clumping, or coagulation, which interferes with the subsequent ability to effectively stain the sample cells. Conversely, if the concentration of alcohol in this embodiment is at 40% or below, the cells are not sufficiently fixed for relatively long-term preservation, causing the cells to degrade over time. In one embodiment, the liquid medium contains approximately 50% methanol, by liquid medium solution. In another embodiment of the invention, the alcohol is present in an amount approximately 20% by liquid medium solution. While this concentration of alcohol, as noted above, does not enable long-term preservation, (i.e., over two days), it does sufficiently fix cells for subsequent analysis. Alternatively, the cells may be transferred from this 20% embodiment solution to a 50% embodiment of the solution, for subsequent long-term preservation prior to analysis.

Another preferred embodiment employs a zinc-based fixative (based on the protocol of Wester et al, Zinc-based fixative improves preservation of genomic DNA and proteins in histoprocessing of human tissues. Lab Invest., 2003. 83(6): p. 889-99). It was found by the inventors that the latter give very satisfying results when combined with the labelled biomarker probe, e.g. an antibody against E6 or E7, p16 or annexin.

The liquid medium according to the current invention also contains an anti-clumping agent in an amount sufficient to prevent cell clumping, preferably by solubilising mucus. In one embodiment, the anti-clumping agent is the chelating agent ethylene diamine tetraacetate (EDTA), with the preferred form being the disodium salt. Other chelating agents deemed useful as the anti-clumping agent include DTT, EGTA, trypsin, cuminin, heparin, streptokinase, and such agents found in lysing or anticoagulant compositions. In another, preferred embodiment, said anti-clumping agent comprises N-acetyl cysteine or N-methyl cysteine.

The buffer used in the inventive solution has a large buffering range to accommodate for the change in pH resulting from autolytic by-products from the sample cells suspended in the solution. For example, as cervical cells age, they release autolytic by-products that alter the pH balance of the suspension solution. In addition, the preservation of different cell types may require solutions of different acidity and within different pH ranges. Accordingly, a solution having a broad buffering range can be used for a wide range of cell types and is optimal for the solution of the invention. Exemplary cells for which this solution can be used include cervical cells, blood cells, bronchial cells, and sputum, among others.

A preferred buffering agent is an acetate buffer, such as sodium acetate, magnesium acetate, calcium acetate, and combinations thereof. Other preferred buffers, include phosphate or Tris buffers, such as for instance phosphate buffered saline (PBS). Preferably, the pH of the liquid medium will be between 2 and 7.

In one embodiment, the preservation time for cells in the present solution, at ambient temperature (approximately 25° C. to 37° C.), is approximately three weeks. This duration may be altered by both the stored age of the solution prior to ambient cell suspension, the amount of time between cell sampling and cell suspension, and the alcohol content. For example, if the solution has been stored for a significant length of time, in either a refrigerated state or an ambient state, then the remaining cell-preserving viability of the solution may be limited.

The liquid medium may furthermore comprise anti-bacterial agents such as antibiotics.

In some instances, the liquid medium may comprise a permeabilizing reagent. Permeabilizing reagents of interest are reagents that allow the labelled biomarker probes, e.g., as described in greater detail below, to access to the intracellular environment. Any convenient permeabilizing reagent may be employed, where suitable reagents include, but are not limited to: mild detergents, such as Triton X-100, Tween, NP-40, Igepal CA-630, N-Octyl-Gluoosid, saponin, etc.; methanol, and the like. It may also be desirable to label cells with a positive heavy metal control, e.g. a DNA intercalator labelled with a heavy metal, e.g. iridium, etc.

The liquid medium may furthermore also comprise a viability dye to stain the cells in said sample, e.g. ethidium bromide, propidium iodide, DAPI, RhCl3, etc.

The means for labelling cells or epitope(s) of the liquid medium according to the current invention comprise a labelled biomarker probe. Said labelled biomarker probe include nucleic acid analytes such as RNA or DNA probes, a protein or a protein analyte, such as an antibody or an antibody fragment, or any custom-made or engineered protein able to bound to or detect an epitope. As reviewed above, the sample that is assayed to obtain morphological and biomarker data is a biomarker labelled sample. Accordingly, the sample is one that has been labelled for one or more biomarkers of interest. By "biomarker labelled sample" is meant a sample which has been contacted with a labelled biomarker probe (e.g., as described in greater detail below) that specifically binds to a biomarker of interest if the biomarker is present in the cellular sample. Biomarkers of interest include, but are not limited to, cervical cancer biomarkers. Cervical cancer biomarkers are a distinctive biological or biologically derived indicator, for example nucleic acids or proteins, whose presence is associated or linked with either the propensity of a subject to develop cervical cancer or the presence of cervical cancer in a subject. Accordingly, biomarkers of interest include nucleic acid and protein analytes whose presence and/or amount in a cell can be used to make a prediction of at least the propensity of a subject to suffer from cervical cancer. Biomarkers of interest include, but are not limited to: HPV expression products of HPV genes, such as HPV genes L1, L2, E2, E4, E5, E6 or E7; cyclin-dependent kinase inhibitors, e.g., p14Arf, p15INK4b, p16 (i.e., p16INK4a as described in Serrano, M., et al., Nature, 1993 Dec. 16; 366(6456): 704-7), p18INK4c, p19INK4d, p21WAF1/CIP1 and p27KIP1; cell cycle regulatory proteins, e.g., p14ARF; annexins such as annexin A1, A2 or A5; specific microRNAs or chromosome alterations 3q-associated with cervical cancer, etc.

Depending on the particular assay to be performed, the liquid medium may be combined with a single labelled biomarker probe or two or more distinct labelled biomarker probes that bind to different biomarkers of different molecular composition, where the number of such distinct labelled biomarker probes may be two or more, e.g., three or more, four or more, five or more, etc; e.g., where the assay is a multiplex assay for two or more biomarkers. In contacting the initial sample with the labelled biomarker probe(s), the sample is combined with one or more labelled biomarker probes to produce a reaction mixture.

Labelled biomarker probes of interest include a specific binding domain and a label domain. The specific binding domain comprises a capture ligand that specifically binds to the biomarker of interest. Depending on the particular assay, the biomarker of interest may be a variety of different types of molecules, including but not limited to: proteins, polypeptides, proteoglycans, glycoproteins and the respective fragments of these molecules; nucleic acids, e.g., DNA and RNA, such as mRNA, etc. The capture ligand is therefore a ligand that binds to the biomarker molecule of interest, wherein this capture ligand may of course vary depending on the specific type of biomarker molecule to be detected, e.g., antibody for protein biomarker, oligonucleotide for mRNA biomarker. In certain embodiments, the affinity between a capture ligand and the biomarker molecule to which it specifically binds when they are specifically bound to each other in a binding or less, $10^{-8}$ M or less, $10^{-9}$ M or less, $10^{-19}$ M or less, $10^{-11}$M or less, $10^{-12}$ M or complex is characterized by a Kd (dissociation constant) of $10^{-6}$ M or less, $10^{-7}$ M less, $10^{-13}$ M or less, $10^{-14}$ M or less, including $10^{-15}$ M or less. Said Kd value can be measured be any conventional method known in the art, such as, but not limiting to, surface plasmon resonance.

As indicated above, a variety of different types of specific binding agents may be employed as the capture ligands, where the particular type of binding agent is selected based, at least in part, on the particular type of molecule of the biomarker of interest.

Specific biomarker probes of interest include antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. Furthermore, said antibody binding agent might be conjugated to nanoparticles, such as for instance magnetic, silver or gold nanoparticles, as described in EP 1 658 497 or EP 1 740 951.

Nucleic acid binding agents of interest are nucleic acids that specifically bind to biomarker nucleic acids in a cell. The length of these nucleic acids may vary, so long as it is sufficient for the oligonucleotide to serve as a specific binding agent, and in some instances ranges from 13 to 100 nt, such as 14 to 50 nt, e.g., 15 to 25 nt. The oligonucleotides that make up these nucleic acid binding agents may be DNA or RNA, or a synthetic analogue thereof, as desired.

In addition to the specific binding domain, the labelled biomarker probes further include a detectable label. Said detectable label might be directly bound on the biomarker probe (primary label) or indirectly bound, e.g. in the case where said biomarker probe comprises an antibody, by a labelled secondary antibody, directed against said biomarker probe (secondary label). Of interest as detectable labels are fluorescent dyes. Fluorescent dyes (fluorophores) can be selected from any of the many dyes suitable for use in imaging applications. A large number of dyes are commercially available from a variety of sources, such as, for example, Molecular Probes (Eugene, Oreg.) and Exciton (Dayton, Ohio). Examples of fluorophores of interest include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow;

Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

Other detectable labels of interest are metal-based labels, such as polymer-coated gold or silver coated nanoparticles. Examples of such labels are given in EP1740951 and EP165849.

Where multiple distinct labelled biomarker probes are employed, the label of each distinct probe may be chosen to provide a distinguishable signal. For example, in embodiments where first and second distinct labelled biomarker probes are employed, e.g. fluorescent labels, the label in the second probe is a fluorescent label which produces a fluorescent signal that is distinguishable from the first fluorescent signal of the label of the first probe. Accordingly, the first and second fluorescent signals produced upon excitation of the first and second fluorescent labels are distinguishable from each other, meaning that both can be detected at the same time and that the signal from one does not modify or change the signal from the other. Each distinct label may produce signals that are distinguishable from any other label. For example, the cells may be stained with a third fluorescent label which produces a third fluorescent signal that is distinguishable from the first and second fluorescent signals.

By preference, said labelled biomarker probe is directed to a biomarker which is known to be upregulated in cancer cells, or which presence is connected to the malignant status of a cell or gives a predisposition to possible malignancy.

For instance, when said cell sample is of cervical origin, the labelled biomarker probe that is employed can be directed to p16INK4a, Ki-67, annexin A5 or HPV E6, E7 labelled probe. Both p16INK4a, Ki-67 or annexin A5 expression are correlated to malignancy in cervical cells (e.g. Li et al., 2012, Mol. Med. Report, Sep. 12 2012; Cavalcante et al., 2012, Indian J Pathol Microbiol, July; 55(3):339-45-2). Expression of HPV viral proteins E6 and E7 are equally correlated with a predisposition to dysplasia. Exemplary probe sequences specific for HPV E6/E7 protein include for instance those described in US 2007 016 669 9, WO 2006 085 822 or US 2012 014 150 2.

Non-limiting examples of components to which cancer or several hereditary conditions are associated with are provided in the following list and, one or more of which are detectable using the method of the invention. A diagnosis may require detection of one or more of the listed molecules comprising of BRCA1, TP53, CFTR, APP, APOE, BRCA2, HBB, APC, MYC, HD, BCL2, ABL1, BAX, DMD, p16INK4A, ATM, TNF, RB1, VEGF, ERBB2, FGG, HPRT1, MAPT, MDM2, RUNX1, SOD1, CDKN1A (cyclin-dependent kinase inhibitor 1A), PAX6, NF1, fibronectin 1, caspase 3, phenylalanine hydroxylase, glyceraldehyde-3-phosphate dehydrogenase, phosphatase and tensin homolog (mutated in multiple advanced cancers 1), hemochromatosis, FGFR3 fibroblast growth factor receptor 3, EGFR epidermal growth factor receptor, MLH1 mutL homolog 1, colon cancer, nonpolyposis type 2, PABPC1 poly(A) binding protein, cytoplasmic 1, CYP3A5 cytochrome P450, subfamily 111A (niphedipine oxidase), MSH2 mutS homolog 2, colon cancer, nonpolyposistype 1, AKT1 v-akt murinethymoma viral oncogene homolog 1, CCND1 cyclin D1 (PRAD1: parathyroid adenomatosis 1), MTHFR 5,10-methylenetetrahydrofolate reductase (NADPH), TGFB1 transforming growth factor, beta 1, IL6 interleukin 6 (interferon, beta 2), KRAS2 v-Ki-ras2 Kirsten rat sarcoma 2 viral oncogene homolog, HRAS v-Ha-ras Harvey rat sarcoma viral oncogene homolog, ret proto-oncogene (multiple endocrine neoplasia and medullary thyroid carcinoma 1, Hirschsprung disease), PPARG peroxisome proliferative activated receptor gamma, ACTB beta-actin, CDH1 cadherin 1, type 1, E-cadherin, ESR1 estrogen receptor 1, IGF1 insulin-like growth factor 1, GSTP1 glutathione S-transferase pi, IL8 interleukin 8, LPL lipoprotein lipase, WT1 Wilms tumor 1 IL1B interleukin 1 beta, CYP1A1 cytochrome P450, CTNNB1 catenin (cadherin-associated protein), ITG A5 integrin, alpha 5 (fibronectin receptor, alpha polypeptide), FOS v-fos FBJ murine osteosarcoma viral oncogene homolog, KIT v-kit Hardy-Zuckerman 4 feline sarcoma viral oncogene homolog, ATP7B ATPase, IGF2 insulin-like growth factor 2 (somatomedin A), JUN v-jun sarcoma virus 17 oncogene homolog, CYP2C19 cytochrome P450, subfamily IIC (mephenyloin 4-hydroxylase), BCR breakpoint cluster region, FGFR2 fibroblast growth factor receptor 2, CASP8 caspase 8, INSR insulin receptor, G6PD glucose-6-phosphate dehydrogenase, IL4 interleukin 4, DRD2 dopamine receptor D2, FGFR1 fibroblast growth factor receptor 1, COL1A1 collagen, type I, alpha 1, BLM Bloom syndrome, NF2 neurofibromin 2 (bilateral acoustic neuroma), MMPI matrix metalloproteinase 1, 1L2 interleukin 2, GRB2 growth factor receptor-bound protein 2, BCL2L1 BCL2-like 1, PSEN2 presenilin 2, TNFRSF6 tumor necrosis factor receptor superfamily, CD44 CD44 antigen, MMP9 matrix metalloproteinase 9, ABCB1 ATP-binding cassette, sub-family B, GSTM1 glutathione S-transferase M1, IL1A interleukin 1, alpha, MET met proto-oncogene (hepatocyte growth factor receptor), B, alpha 1-3-galactosyltransferase), NRAS neuroblastoma RAS viral (v-ras) oncogene homolog, NAT2 N-acetyltransferase 2 (arylamine Nacetyltransferase), EGR1 early growth response 1, TTR transthyretin (prealbumin, amyloidosis type I), SOD2 superoxide dismutase 2, mitochondrial, SCYA2 small inducible cytokine A2 (monocyte chemotactic protein 1), NOS3 nitric oxide synthase 3 (endothelial cell), CDC2 cell division cycle 2, G1 to S and G2 to M, STAT1 signal transducer and activator of transcription, SNCA synuclein, alpha (non A4 component of amyloidprecursor), CLU clusterin, CDKN1B cyclin-dependent kinase inhibitor 1B (p27, Kip1), TYR tyrosinase (oculocutaneous albinism IA), CDK2 cyclin-dependent kinase 2, MMP3 matrix metalloproteinase 3, YWHAZ tyrosine 3-monooxygenase/tryptophan 5-monooxygenase activation protein, zetapolypeptide, CASP1 caspase 1, apoptosis-related cysteine protease, PCNA proliferating cell nuclear antigen, HLA-A, -B, -C major histocompatibility complex, class I, A, B, C, APOB apolipoprotein B (including Ag(x) antigen), CASP9 caspase 9, apoptosis-related cysteine protease, NOS2A nitric oxide synthase 2A, IFNG interferon, gamma, APOA1 apolipoprotein A-1, AGT angiotensinogen, ADA adenosine deaminase, ICAM1 intercellular adhesion molecule 1 (CD54), CYP19 cytochrome P450, subfamily XIX, SLC6A4 solute carrier family 6 (neurotransmitter transporter, serotonin), member 4, TNFRSF1A tumor necrosis factor receptor superfamily, member 1A, CD4 CD4 antigen (p55), VWF von Willebrand factor, ACTA1 actin, alpha 1, COMT catechol-O-methyltransferase, TERT telomerase reverse transcriptase, PKD polycystic kidney disease 1, F7 coagulation factor VII (serum prothrombin conversion accelerator), PMP22 peripheral myelin protein 22, F5 coagulation factor V (proaccelerin, labile factor), PPARα peroxisome proliferative activated receptor, alpha, GCK glucokinase (hexokinase 4, maturity onset diabetes of the young 2), MUC1 mucin 1, transmembrane, SPP1 secreted phosphoprotein 1, RAF1v-raf-1 murine leukemia viral oncogene homolog 1, IGF1R insulin-like growth factor 1 receptor, IL4R interleukin 4 receptor, DCC deleted in colorectal carcinoma, PML promyelocytic leukemia, PDGFRB platelet-derived growth factor receptor, beta polypeptide, AGTR1 angiotensin receptor 1, UBE3A ubiquitin protein ligase E3A (human papilloma virus E6-associated protein, Angelman syndrome), CREBBP CREB binding protein, CYP1B1 cytochrome P450, subfamily. AKT2 v-akt murine thymoma viral oncogene homolog 2, PLAT plasminogen activator, tissue, CHRNA7 cholinergic receptor, nicotinic, alpha polypeptide 7, TIMP1 tissue inhibitorof metalloproteinase 1 (erythroId potentiating activity, collagenase inhibitor), NFKB1 nuclear factor of kappa light polypeptide gene enhancer in B-cells 1 (p105), STAT3 signal transducer and activator of transcription 3 (acute-phase response factor), CDC42 cell division cycle 42 (GTP binding protein, 25 kD), VDR vitamin D (1,25-dihydroxyvitamin D3) receptor, NTRK1 neurotrophic tyrosine kinase, receptor, type 1, VIM vimentin, TGFBR2 transforming growth factor, beta receptor II, DHFR dihydrofolate reductase, CYP2A6 cytochrome P450, subfamily IIA, HSPCA heat shock 90 kD protein 1, alpha, E2F1E2F transcription factor 1, CACNA1A calcium channel, voltage-dependent, P/Q type, LCK lymphocyte-specific protein tyrosine kinase, LGALS3 lectin, galactoside-binding, soluble, 3 (galectin 3), RARA retinoic acid receptor, alpha, PDZK1 PDZ domain containing 1, ALDH2 aldehyde dehydrogenase 2 family, PAX3 paired box gene 3 (Waardenburg syndrome 1), FGF2 fibroblast growth factor 2 (basic), GJB1 gap junction protein, beta 1, LMNA lamin A/C, CAPN3 calpain 3, ADPRT ADP-ribosyltransferase (NAD-1-; poly, TUBB tubulin, beta polypeptide, ABCA1 ATP-binding cassette, sub-family A (ABC1), IL1RN interleukin 1 receptorantagonist, CTGF connective tissue growth factor, GSTT1 glutathione S-transferase theta 1, DRD4 dopamine receptor D4, HTR2A 5-hydroxytryptamine (serotonin) receptor 2A, FHIT fragile histidine triad gene, ETV6 ets variant gene 6 (TEL oncogene), PDGFB platelet-derived growth factor beta polypeptide (simian sarcoma viral (v-sis) oncogene homolog), PPP3R1 protein phosphatase 3 (formerly 2B), TIM P3 tissue inhibitor of metalloproteinase, COL1A2 collagen, type I, alpha 2, ITG B3 integrin, beta 3, COL3A1 collagen, type III, alpha 1 (Ehlers-Danlos syndrome type IV, autosomal dominant), ESR2 estrogen receptor 2 (ER beta), B2M beta-2-microglobulin, SDF1 stromal cell-derived factor 1, F9 coagulation factor IX, MAPK14 mitogen-activated protein kinase 14, BAK1 BCL2-antagonistlkiller 1, ITGB1 Integrin, beta 1, ACTG1 actin, gamma 1, KDR kinase insert domain receptor (a type III receptor tyrosine kinase), SCTR secretin receptor, LEPR leptin receptor, SP1 Sp1 transcription factor, CDKN1C cyclin-dependent kinase inhibitor 1C (p57,Kip2), MYCN v-myc myelocytomatosis viral related oncogene, IL 12B interleukin 12B, IGF2R insulin-like growth factor 2 receptor, FLT1 fms-related tyrosine kinase, CD36 CD36 antigen (collagen type I receptor, thrombospondin receptor), FRD Friedreich ataxia, COL2A1 collagen, type II, alpha 1, GSN gelsolin (amyloidosis, Finnish type), CYP2E cytochrome P450, subfamily IIE, APAF1 apoptotic protease activating factor, ANK1 ankyrin 1,SLC6A3 solute carrier family 6, CASP7 caspase 7, apoptosls-related cysteine protease, MYH7 myosin, heavy polypeptide 7, JUNB jun B proto-oncogene, GHR growth hormone receptor, IRS1 insulin receptor substrate 1, CASP10 caspase 10, apoptosis-related cysteine protease, BDNF brain-derived neurotrophic factor, ATP7A ATPase, Cu++ transporting, alpha polypeptide (Menkes syndrome), TCF1 transcription factor 1, HGF hepatocyte growth factor, CYP17 cytochrome P450, subfamily XVII (steroid 17-alpha-hydroxylase), adrenal hyperplasia, PTPN1 protein tyrosine phosphatase, ADRB3 adrenergic, beta-3-, receptor, TNFSF6 tumor necrosis factor (ligand) superfamily, VCAM1 vascular cell adhesion molecule 1, TF transferrin, ACE angiotensin I converting enzyme, LRP1 low density lipoprotein-related protein 1, CDK5 cyclin-dependent kinase 5, ACACA acetyl-Coenzyme A carboxylase alpha, TNFRSF1B tumor necrosis factor receptor superfamily, ERBB3 v-erb-b2 erythroblastic leukemia viral oncogene homolog 3, CSK c-src tyrosine kinase, SCN5A sodium channel, BCL6 B-cell CLIIlymphoma 6, CTSK cathepsin K, SPARC secreted protein, acidic, cysteine-rich, NFKB2 nuclear factor of kappa light polypeptide gene enhancer in B-cells 2, SCYA5 small inducible cytokine A5 (RANTES), BMP4 bone morphogenetic protein 4, ATP2A2 ATPase, NR3C1 nuclear receptor subfamily 3, THBS1 thrombospondin 1, CETP cholesteryl ester transfer protein, PTPRC protein tyrosine phosphatase, receptor type, TGFBI transforming growth factor, beta-induced, SREBF1 sterol regulatory element binding transcription factor 1, MMP14 matrix metalloproteinase 14, KCNQ1 potassium voltage-gated channel, KQT-like subfamily, member 1, TUBA1 tubulin, alpha 1 (testis specific), SELE selectin E (endothelial adhesion molecule 1), IL2RG interleukin 2 receptor, IGFBP3 insulin-like growth factor binding protein 3, JAK3 Janus kinase 3, CSF1R colony stimulating factor 1 receptor, SHC1 SHC (Src homology 2 domain containing) transforming protein 1, CASP4 caspase 4, apoptosis-related cysteine protease, PLA2G2A phospholipase A2, group 11A, CXCR4 chemokine (C-X-C motif), receptor 4, CDKN2B cyclin-dependent kinase inhibitor 2B, ARHA ras homolog gene family, member A, SHH sonic hedgehog homolog, RARB retinoic acid receptor, MME membrane metallo-endopeptidase, CA2 carbonic an hydrase II, PRKDC protein kinase, DNA-activated, catalytic Polypeptide, HIF1A hypoxia-Inducible factor 1, PRKCA protein kinase C, CASP2 caspase 2, apoptosis-relatedcysteine protease, DMBT1 deleted in malignant brain tumors 1, TGFB2 transforming growth factor, beta 2, TSC2 tuberous sclerosis 2, PSAP prosaposin, XPC xeroderma pigmentosum, THRA thyroid hormone receptor, alpha (erythroblastic leukemia viral (v-erb-a), ERCC2 excision repair cross-complementing rodent repair deficiency, complementation group 2, MAPK1 mitogen-activated protein kinase 1, ATP6B1 ATPase, BAG1 BCL2-associated athanogene, ACHE acetylcholinesterase (YT blood group), EGF epidermal growth factor (beta-urogastrone), DUSP1 dual specificity phosphatase 1, CASP6 caspase 6, apoptosis-related cysteine protease, THRB thyroid hormone receptor, BAD BCL2-antagonist of cell death, STAT6 signal transducer and activator of transcription 6, ELN elastin, MAOA monoamine oxidase A, F8 coagulation factor VIII, procoagulant component, ENG endoglin, HSPB1 heat shock 27 kD protein 1, HMGCR 3-hydroxy-3-methylglutaryl-Coenzyme A reductase, PIM1 pim-1 oncogene, PON1 paraoxonase 1, AHR aryl hydrocarbon receptor, ITGB2 integrin, beta 2, GS1 prostaglandin-endoperoxide synthase 1(prostaglandin G/Hsynthase and cyclooxygenase), CG1 phospholipase C, gamma 1 (formerly subtype 148), APOC3 apolipoprotein C-III, NRG1 neuregulin 1, CD14 CD14 antigen, IRF1 interferon regulatory factor 1, ALPL alkaline phosphatase, liver/bone/kidney, ALDOA aldolase A, fructose-bisphosphate, PDGFRA platelet-derived growth factor receptor, IL5 interleukin 5, BMP2 bone morphogenetic protein 2, GSK3A glycogen synthase kinase 3 alpha, STK11 serine/threonine kinase 11, GSK3B glycogen synthase kinase 3 beta, CRYBB1 crystallin, beta B1, STAT5A signal transducer and activator of transcription 5A, SCA1 spinocerebellar ataxia 1 (olivopontocerebellar ataxia 1, autosomal dominant, ataxin 1), RXRA retinoid X receptor, NFKBIA nuclear factor of kappa light polypeptide gene, enhancer in B-cells inhibitor, alpha, MMP13 matrix metalloproteinase 13 (collagenase 3), TSHR thyroid stimulating hormone receptor, MT2A metallothionein 2A, TSSC3 tumor suppressing subtransferable candidate 3, RHO rhodopsin, GADD45A growth arrest and DNA-damage-inducible, LCAT lecithin-cholesterol acyftransferase, GSR glutathione reductase, TOP2A topolsomerase (DNA) II alpha (170 kD), GPX1 glutathione peroxidase 1, FLT3 fms-related tyrosine kinase 3, CEBPB CCAAT/enhancer binding protein (C/EBP), TPM1 tropomyosin 1, ABCA4 ATP-binding cassette, sub-family A (ABC1), KCNH2 potassium voltage-gated channel, subfamily H, HNF4A hepatocyte nuclear factor 4, DPYD dihydropyrimidine dehydrogenase, MADH2 MAD, AFP alpha-fetoprotein, TIMP2 tissue inhibitor of metalloproteinase 2, ITK IL2-inducible T-cell kinase, ABL2 v-abl Abelson murine leukemia viral oncogene homolog 2, SCYA4 small inducible cytokine A4, GCGR glucagon receptor, TCF3 transcription factor 3 (E2A immunoglobulin enhancer binding factors E12/E47), LTA lymphotoxin alpha, LIF leukemia inhibitory factor, CYBB cytochrome b-245, beta polypeptide (chronic granulomatous disease), CTSL cathepsin L, BCL2A1 BCL2-related protein Al, TFRC transferrin receptor (p90, CD71), RALGDS ral guanine nucleotide dissociation stimulator, CYP2C8 cytochrome P450, CD38 CD38 antigen (p45), PRKCZ protein kinase C, LAMR1 laminin receptor 1 (67 kD, ribosomal protein SA), IL12A interleukin 12A, FGA fibrinogen, EEF1A1 eukaryotic translation elongation factor 1 alpha1, CYP21A2 cytochrome P450, subfamily XXIA, CSF2 colony stimulating factor 2 (granulocytemacrophage), TNFRSF5 tumor necrosis factor receptor superfamily, MBP myelin basic protein, PTK2 PTK2 protein tyrosine kinase 2, KLK3 kallikrein 3, (prostate specific antigen), GALT galactose-1-phosphate uridylyltransferase, APEX APEX nuclease (multifunctional DNA repair enzyme), EPHB2 EphB2, BIK BCL2-interacting killer (apoptosis-inducing), SLC2A1 solute carrier family 2, IL2RA interleukin 2 receptor, alpha, IFNG R2 interferon gamma receptor2 (interferon gamma transducer 1), AXL AXL receptor tyrosine kinase, ADRB1 adrenergic, beta-1-, receptor, GJA1 gap junction protein, alpha 1, 43 kD (connexin43), EWSR1Ewing sarcoma breakpoint region 1, CCR2 chemokine (C-C motif) receptor 2, RELA v-rel reticuloendotheliosis viral oncogene homolog A, nuclear factor of kappa light polypeptide gene enhancer in B-cells 3, p65, CTNNA1 catenin (cadherin-associated protein), MY07A myosin VIIA, F3 coagulation factor III (thromboplastin, tissue factor), EPHX1 epoxide hydrolase 1, CRK v-crk sarcoma virus CT10 oncogene homolog, EN01 enolase 1, TGFBR1 transforming growth factor, beta receptor I, RAC1 ras-related 03 botulinum toxin substrate 1 (rho family, small GTP binding protein Rac1), ANPEP alanyl (membrane) aminopeptidase.

Additional specific probes that find use in the methods and systems described herein may be designed and tested using any convenient probe design methodology.

Preferably, the means for labeling cells or epitope(s) are provided in a concentration suitable to detect a biomarker present in a sample at a concentration of 500 pg or more. More preferably said biomarker present in a sample is able to detect a biomarker in a sample at a concentration of 250 pg or more, even more preferably of 150 pg or more, more preferably of 100 pg or more, most preferably of 50 pg or more.

Furthermore, the means for labeling cells or epitope(s) on or in said cells are preferably provided in the liquid medium in a concentration between 0.01 µg/ml and 50 µg/ml, more preferably in a concentration between 0.04 µg/ml and 20 µg/ml, more preferably between 0.04 µg/ml and 10 µg/ml, more preferably between 0.04 µg/ml and 5 µg/ml, more preferably between 0.04 µg/ml and 2 µg/ml, more preferably between 0.04 µg/ml and 1 µg/ml, more preferably between 0.08 µg/ml and 0.5 µg/ml, most preferably between 0.2 µg/ml and 0.4 µg/ml.

Contact of the sample with the labelled biomarker probe(s) present in the liquid medium is performed under incubation conditions that provide for binding of probes to their respective biomarkers, if present, in the sample. In some instances, the probes and samples are contacted and combined at a temperature ranging from 15 to 50, such as from 20 to about 40° C. Contact may be performed with mixing or agitation, e.g., with vortexing etc., to provide for sufficient combination of the reaction components and the sample.

The resultant reaction mixture may then be maintained or incubated for a period of time prior to assay for morphological and biomarker data, e.g., via digital holographic microscopy (e.g., as described in greater detail below). In some instances, the reaction mixture is incubated at a temperature ranging from 15 to 50, such as from 20 to about 40° C. for a period of time ranging from about 30 minutes to 72 hours, such as from 1 hour to 24 hours, including 1 hour to 3 hours. Following the above incubation step, the sample may be assayed immediately or stored for assay at a later time. If stored, in some embodiments the sample is stored at a reduced temperature; e.g at 4° C. or below, between −10° C. and −40° C. In some embodiments, as described above, the liquid medium comprises a non-specific cell stain, in addition to a biomarker label. The cells may be stained with a non-specific stain using any convenient protocol. Of interest as non-specific cells stains are DNA specific stains. Dyes and stains that are specific for DNA (or preferentially bind double stranded polynucleotides in contrast to single-stranded polynucleotides) and therefore may be employed as non-specific stains include, but are not limited to: Hoechst 33342 (2'-[4-ethoxyphenyl]-5-[4-methyl-1-piperazinyl]-2, 5'-bi-1H-benzimidazole) and Hoechst 33258 (2'-[4-ethoxyphenyl]-5-[4-methyl-1-piperazinyl]-2,5'-bi-1H-benzimidazole) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyactridine. Depending on the particular stain and assay, the stain may serve in quantitation of biomarker, as an indication of cell cycle, etc.

Following obtainment and suspension of the sample in the liquid medium, e.g., as described above, the sample is assayed to obtain both morphological as well as biomarker and/or non-specific cell data. In a preferred embodiment, analysis occurs in the same aliquot of sample, i.e., the same physical quantity of sample, is assayed to obtain both the morphological and biomarker/non-specific cell data. Obtainment of the data occurs simultaneously, meaning that both the morphological data and the biomarker data are obtained from one sample, with the same device and at the same time-point. Accordingly, these embodiments are distinguished from protocols in the prior art, in which a first aliquot of a sample is assayed using one protocol, e.g., slide based protocol, for morphological data and a second aliquot of the sample is assayed using another protocol. This provides for a more accurate, and less time consuming protocol.

Morphological data refers to any type of data from which cell morphology information, i.e., information about the size, shape and/or structure of the cells, may be derived.

Morphological data or parameters of interest include, but are not limited to: nuclear area, perimeter, texture or spatial frequency content, centroid position, shape (i.e., round, elliptical, barbell-shaped, etc.), volume, optical nuclear height, cell nucleus diameter, chromatin texture, cell size, percent nucleation, cell form, cell quantity, nuclear size, nuclear volume, nuclear size variability, nuclear volume variability, chromatin texture, cell size, nuclear optical density, cytoplasm optical density, background optical density, and ratios of any of these parameters. The obtained morphological date may be for cells as a whole or for subparts thereof, e.g., the cytoplasm of cells. In some instances, the morphological data may include an actual designation of whether a cell is normal or abnormal, including the type of abnormal cell. For example, morphological data may, in some instances, include a designation that a given cell is abnormal, for example that the cell is: an atypical squamous cell, e.g., atypical squamous cell of undetermined significance (ASC-US), atypical squamous cell—cannot exclude HSIL (ASC—H); low grade squamous intraepithelial lesion (LGSIL or LSIL); high grade squamous intraepithelial lesion (HGSIL or HSIL); squamous cell carcinoma; atypical glandular cell not otherwise specified (AGC-NOS); atypical clandular cell, suspicious for AIS or cancer (AGC—neoplastic); and adenocarcinoma in situ (AIS).

Biomarker data refers to any type of data from which biomarker information for the cell may be derived. In some instances, biomarker data is data that includes a signal provided by the label of the labelled biomarker probe that is employed in the assay. The biomarker data may be in the form of the presence and amplitude of emitted light, the number of discrete positions in a cell or other object from which the light signal(s) originate(s), the relative placement of the signal sources, and the colour (wavelength or waveband) of the light emitted at each position in the cell. The biomarker data may take the form of qualitative, semi-quantitative or quantitative data. Qualitative data is simply the presence or absence of the biomarker. Semi-quantitative or quantitative data is data that provides some indication of the amount, e.g., concentration, etc., of the biomarker in the cell. For example, semi-quantitative data may take the form of an indication that a biomarker of interest is above a certain threshold number. Quantitative data provides an indication of an absolute value, e.g., amount, etc., of the biomarker in the cell. Semi-quantitative and quantitative data may be collectively referred to as biomarker quantitation data.

In some instances, the biomarker of interest is a protein that is present when a subject is infected with a high risk HPV strain. Proteins of interest include but are not limiting to HPV E6, E7, L1, L2. In another embodiment, the biomarker of interest is a protein upregulated in cervical cancer or dysplasia. Examples of such proteins include but are not limiting to for instance p16, Ki-67 or annexin A5. In another embodiment, detection of biomarkers of both groups occurs.

Said biomarker data will be retrieved by omitting any background signal due to unbound biomarker probe or aspecific bound biomarker probe. As one of the preferred embodiments of the current invention does not include any washing step or removal of the unbound biomarker probe, deduction of this aspecific signal is indispensable to retrieve reliable information. Deduction of aspecific signal occurs preferably by use of software implementation. In one of the embodiments, threshold information on the background signal and other aspecific signals is standardly stored in said software as a predefined value. Said threshold information can be obtained from a control sample in the liquid medium supplemented with biomarker probe according to the current invention but negative for the presence of the used biomarker. The obtained signal will account as negative background signal and can be used for deduction when predicting the state of subject samples. Samples showing a certain threshold signal after deduction of the background signal can be accounted as positive.

In another embodiment, the background signal will be determined each time a round of analysis starts. Again, a sample known to be negative for the assessed biomarker will be used and the retrieved signal will account as background signal. In another embodiment, cells are isolated from the background (segmented) based on their optical properties and specifically the phase information extracted from the hologram. Hence, the morphological data is isolated from the background originating from unbound biomarker probe, based on phase information retrieved by the digital holographic microscope. This phase information is a quantitative measure of the thickness of the objects present in the image. For example, the background can be defined as an object that has an optical thickness below a given threshold.

The biomarker signal analysis can hence be limited to the regions of the image where objects (cells) are present and the aspecific signals originating from unbound or aspecifically bound biomarker is thereby eliminated.

Non-specific cell data is any type of data from which non-specific (i.e., non-biomarker specific) cell information for the cells in the sample may be derived. In some instances, nonspecific cell data is data that includes a signal emitted by a non-specific cell stain that is employed in the assay. The non-specific cell data may be in the form of the presence and amplitude of emitted light, the number of discrete positions in a cell or other object from which the light signal(s) originate(s), the relative placement of the signal sources, and the color (wavelength or waveband) of the light emitted at each position in the cell. The nonspecific cell data may take the form of qualitative, semi-quantitative or quantitative data. For example, quantitative or semi-quantitative non-specific cell data may include data on the DNA content of a cell obtained using a DNA stain (e.g., as described above). Other quantitative data includes electronic volume (EV). Thus, non-specific cell data may provide an indication of an absolute or relative value, e.g., copy number, amount, etc., of the nonspecific cell component in the cell. Semi-quantitative and quantitative data may be collectively referred to as non-specific cell quantitation data. Qualitative non-specific cell data can provide information with respect to the presence of absence of a particular feature of a cell. For example, in cells stained with a DNA stain, the presence or absence of a cell nucleus can be determined (e.g., the number of nucleated cells in a sample, also referred to as percent nucleation).

It is noted that where multiple distinct labels are to be detected in a single labelled liquid cell sample, e.g., biomarker probe labels and non-specific cell stains used in a single sample, the labels and stains employed may be chosen to provide a distinguishable signal (as described above for using multiple biomarker probes in a single sample, above). For example, in embodiments where a labelled biomarker probe and a DNA stain are employed, the label for the biomarker probe is a fluorescent label which produces a fluorescent signal that is distinguishable from the fluorescent signal of the DNA stain. Accordingly, the fluorescent signals produced upon excitation of the biomarker probe label and the DNA stain are distinguishable from each other, meaning that both can be detected at the same time and that the signal from one does not modify or change the signal from the other. Each distinct label may produce signals that are distinguishable from any other label. For example, the cells may be stained with three fluorescent labels which produce three distinct fluorescent signals that are distinguishable from each other upon excitation.

The above types of data, e.g., the morphological, biomarker, and non-specific cell data, is simultaneously obtained from the same aliquot of sample.

In a preferred embodiment of the current invention, above mentioned types of data is obtained by Digital Holographic Microscopy. Digital Holographic Microscopy (DHM) is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent or a partially coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is exemplified in European patent EP 1 631 788. The DHM used in the current invention can comprise a conventional digital holographic microscope (DHM), or a differential digital holographic microscope (DDHM). It is to be understood that the use of the term DHM in the current application implies all types of digital holographic microscopes, and is not merely limited to conventional DHM.

The use of DHM in a diagnostic setting has many advantages which makes it the ideal technique to implement in a diagnostic setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological cells, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. Digital holographic microscopy thus makes it possible to visualize and quantify transparent objects and is therefore also referred to as quantitative phase contrast microscopy. More so, DHM allows imaging subcellular structures in three dimensions.

A sample image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object. Furthermore, as DHM systems do not have an image forming lens, traditional optical aberrations do not apply to DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost.

In the methods and systems according to the current invention, use of DHM allows obtaining both two-dimensional and three-dimensional morphological data of the cell sample, as well as biomarker data, preferably based on fluorescent technology. Preferably, a digital report is created comprising all obtained data linked to a sample, as well as identification data related to said sample and ID of the subject. Said digital report will comprise morphological data, comprising both detailed two-dimensional and three-dimensional images of the sample and cells within sample, as well as quantitative information on cell parameters as described above. Said digital report will furthermore comprise biomarker data, such as biomarker signal measured, information on background signal and threshold values defining presence or absence of for instance HPV infection.

In an embodiment, morphological and biomarker/non-specific cell data obtained from the same aliquot of cervical cellular sample, e.g., as described above, is employed to predict whether the cell sample of the subject comprises cancerous or pre-cancerous cells.

In a more preferred embodiment, at least one cellular parameter derived from obtained holographic information comprises the optical nuclear height or optical height delta. The optical nuclear height or optical height delta, can be defined as the difference between Nucleus top height minus Cytoplasm average height and is preferably derived from the obtained holographic information. It has been found by the inventors that the latter is a highly reliable parameter for detecting (pre-) cancerous cell and that it can be correlated to the status of malignancy of said cells.

Various combinations of morphological, biomarker, and non-specific cell data may be employed in making a prediction of whether a subject has a CIN lesion.

Combinations of interest include, but are not limited to, the following: a) nuclear to cytoplasmic (N/C) ratio analysis (e.g., to identify abnormal cells) coupled with the presence of for instance E6, E7 or p16 biomarkers; b) N/C ratio analysis coupled with cell cycle analysis as determined by DAPI staining and fluorescence signal of for instance E6, E7 or p16 presence; c) N/C ratio analysis coupled with cell cycle analysis as determined by p16 staining and green fluorescence of the E6, E7 mRNA hybridization signal; d) N/C ratio analysis coupled with cell cycle analysis as determined by DAPI (or other DNA stain) staining, etc.

Increased, or high, N/C ratios include N/C ratios that are 0.25 or higher, 0.30 or higher, 0.4 or higher, 0.5 or higher, 0.6 or higher, 0.7 or higher, 0.8 or higher, 0.9 or higher, 0.95 or higher, etc.

In addition to N/C ratio, nuclear area (NA) assessment may be used as morphological data. Cells in a cervical cell sample having an increased nuclear area, e.g., as compared to nuclei in normal intermediate squamous cells, can be identified cells as abnormal cells. Abnormal cells may have a nuclear area-to-nuclear area ratio (nuclear area of cell of interest/nuclear area of normal intermediate squamous cell) of 1.25 or more, 1.75 or more, 2.0 or more, 2.25 or more, 2.75 or more, 3.0 or more, 3.25 or more, 3.5 or more, etc. It is noted here that using standard microscopy observations, the accuracy of estimating nuclear area is low (see, e.g., Schmidt et al., 2008, "Visual estimates of nucleus-to-nucleus ratios: can we trust our eyes to use the Bethesda ASCUS and LSIL size criteria?" Cancer 1 14(5):287-93. Aspects of the present invention provide a more accurate and reproducible assessment of nuclear area.

In some instances, the methods include determining that the assayed cellular sample includes cancerous cells. In these embodiments, the methods include identifying the presence of one or more cancerous cells in the sample, where the identification is made based on morphological and biomarker data, e.g., as described above. Such embodiments may or may not include predicting the presence of CIN in a subject, since the methods of these embodiments identify the presence of actual cancerous cells in the sample.

The method preferably includes a step whereby the obtained data is compared and correlated to a threshold database comprising a set of thresholds related to known cellular parameters in order to classify or predict the health status of said cells. The term "threshold database" as used herein refers to any suitable collection of reference information or reference parameters related to a sample. Said threshold database comprises at least one of the above mentioned morphological parameters and may include data on cell size, cell morphology, number of cells in a defined area, optical density of the nucleus of cell, optical height of nucleus, optical height of the cytoplasm, ratio between optical height nucleus and cytoplasm, ratio between cytoplasm and nucleus of a cell, colour of a cell, colour of a nucleus, colour of a cell wall, number and form of internal cellular structures like the number and form of vacuoles, the number and form of mitochondria, division related structures like chromosomal structures, form, size, morphology of the nucleus and/or the location of the nucleus within the cell, association of cells, the degree of independence of cells, volume of a cell, proportion of the length of the cell wall to the cell size, number of identical or similar cells in an image, or number of ruptures, fissures, holes or visible pores in a cell. The corresponding information may be stored in any suitable format. Furthermore, said threshold database includes information on biomarker thresholds in cells. For instance, said threshold database might comprise a threshold value regarding the presence or absence of HPV infection in said cells, based on the detected signal of the biomarker. Above a certain detected threshold, one can with high certainty state that infection is present in the cells.

Preferably, said threshold database also comprises information on the background signal of unbound biomarker probe. Said information on background signal will depend on the used concentration range of the biomarker probe. Hence, the effective biomarker data will obtained by omitting or retracting the background signal resulting from unbound biomarker probe from the overall detected biomarker signal.

The reference parameters or the reference information on morphological parameters and biomarker information may be stored in the form of predefined threshold values, which allow a fast and reliable comparison of measured values with predefined default values.

In one embodiment, a prediction or diagnosis is appointed to the entire sample or constituents of said sample, based upon the comparison of the obtained data with said data stored in the threshold database. Said prediction or diagnosis is appointed by use of queries.

In one embodiment, said threshold database can be stored locally on an internal server, for instance directly accessible by the practitioner analysing said cell sample. This way the practitioner can consult his own version of the database stored on his computer or internal server. In a more preferred embodiment, said threshold database is stored on an external server, which requires sending the obtained holographic information to said external server. Said prediction is achieved by use of queries on said internal or external server. In another more preferred embodiment, said database and queries are applicable for cloud computing and being stored and/or computed in the cloud.

In one of the further embodiments, a practitioner presented with the analysis and prediction of the sample can indicate whether in his opinion, the prediction appointed to said sample, cells or cell types in sample matches with his diagnosis, equally based on retrieved data by DHM but independent from the queries and threshold database information. This opinion will be resend to said external server where the opinion of the practitioner can be compared to the opinion provided by the server. The latter will serve as a constant quality control of the threshold database and the algorithms used for analysis and provides for a dynamic system as the threshold database and the algorithms will be constantly adapted and updated, based on the findings of said practitioners. As such, an intelligent, self-sustaining database is created.

In another, more preferred embodiment, the method according to the current invention will allow the concept of "collaborative diagnostics". For the current invention, the term "collaborative diagnostics" is to be understood as a diagnostic method, whereby the diagnosis of a sample, preferably a cell sample, is retrieved by a collaboration of professionals in a relevant field of interest (e.g. pathologists, medical doctors, scientists, etc.), whereby each said professional is able to give an opinion or state a diagnosis related to the sample, based on the data retrieved by the DHM. Said professional can be independent and does not have to be professionally linked to the patient, cell sample or practitioner that obtained the cell sample. Said professional can retrieve the data from a remote location (a collaborative diagnostic platform) and provide an independent opinion/diagnosis on the status of the sample. Said diagnosis is then communicated to the practitioner in charge of the final diagnosis of the sample and/or to other professionals, member of the collaborative diagnostic platform. As such, the final diagnosis may be based on both the opinion/diagnosis of the practitioner directly related to patient and sample, and on the opinion/diagnosis of the external professionals.

Preferably, said threshold database will be an intelligent, self-sustaining database, based on the input from the practitioner and from professionals providing an opinion/diagnosis on said sample.

In some instances, the methods further include performing further analysis of a subject if the methods result in a prediction of the presence of cancerous cells in the subject. For example, where methods of the invention result in prediction of a CIN2+ lesion in a subject, the methods may then further include providing a recommendation to a subject that further action be taken, e.g., in the form of further diagnostic procedures, such as biopsy. In some instances, the methods include taking further diagnostic action. Further diagnostic action may include a colposcopy, in which a magnified visual inspection of the cervix is performed to identify abnormal cells on the surface of the cervix. If the biopsy indicates that cancer or pre-cancerous lesions may be present, further diagnostic and treatment procedures may be taken, such as loop electrical excision procedure (LEEP) and conization, in which the inner lining of the cervix is removed to be examined pathologically. While the methods are suitable for use with a variety of different female mammalian subjects, of interest are use of the methods with human female subjects, such as human female subjects of 10 years age or older, e.g., 15 years age or older, including 20 years age or older.

Current invention equally provides for a specially designed sample vial, for collecting and preservation of the sample in the liquid medium and suitable for the method according to the current invention. The sample vial according to the current invention preferable comprises at least two compartments in fluid connection with one another, said compartments comprising at least one pair of screening surfaces, said screening surfaces are essentially flat; whereby the distance between the pair of screening surfaces of the second compartment is smaller than the distance between the pair of screening surfaces of the first compartment.

The term 'screening surfaces' as used in current invention is to be understood of the specific area of the vial which is at the inner side of the vial in contact with the sample and whereby said area is suitable for passage of a light beam in order to create a hologram of the sample.

As used herein, the distance between the pair of screening surfaces is to be understood as the inner-distance measured at the inside of said sample vial between two opposite points of said pair of screening surfaces. Preferably, especially for the second compartment, said opposite points of pair of screening surfaces are, when vial is filled with a sample, in contact with said sample. Preferably, said distance is the shortest distance that can be measured between two opposite points of said pair of screening surfaces (see FIG. 2a).

By making the distance of the screening surfaces of the first compartment larger than the distance of the screening surfaces of the second compartment, one can establish different cell densities within the same vial. Obtaining an optimal cell density is from crucial importance when wanting to analyse cells, especially from a suspension, when cells are mostly free-floating cells in a liquid cell sample. When said sample vial is immobile, allowing cells to settle by gravitation, typically more dense concentrations of cells will be found at the centre of the bottom of the first compartment compared to the cell density in the second compartment, whereby the nature of the cell density is determined by the distance between the pair of screening surfaces of each compartment. Typically, the density obtained in the second compartment, will closely mimic the cell density that is obtained with thin cell layer techniques, whereby cells originating from a liquid cell sample are deposited on an analytical carrier such as a microscope slide by for instance centrifugation forces or gravity force. The current sample vial omits all handling steps which precede the acquirement of such a thin cell layer, hence gaining time and money. Alternatively, when said sample vial is subjected to a rotational movement, preferably along a vertical axis of the vial, the cell density may be higher at the periphery of the first compartment and in the second compartment of the vial. The sample vial according the current invention provides for at least two different cell densities within the same sample vial. The chosen distance between each pair of screening surfaces of each compartment will vary according to the type of cell sample that is to be analysed and is linked to the minimal cell density known to be required for analysing such a cell sample. Simultaneously, the nature of the cell sample as well as the purpose of the analysis will define which pair of screening surfaces is to be used for the analysis by DHM. For instance, when a cell sample is composed of various sorts of cells, whereby only a specific subset of cells is important to the analysis, one can deduct in which compartment the latter are enriched, hence only focusing on that specific compartment. When the purpose of the analysis requires a high cell density of cells, screening can be performed through the pair of screening surfaces of said compartment with the highest distance between the latter, typically at the centre of the bottom of the first compartment. Focusing on the compartment with the highest cell density will furthermore also limit the amount of images or fields of view required for coming to an adequate and significant analysis. Alternatively, when the cells in this field are too dense to perform an adequate analysis, and a high transparency is desired, screening can be performed through the pair of screening surfaces of the second compartment, in the situation where the sample vial is immobile. Again, the latter will depend on the nature of the cell sample, the cell quantity required for an optimal cell analysis and the purpose of the analysis. Furthermore, by applying the distant-ratio's as disclosed herein, cells will become immobilized in the second compartment of the vial in a very short amount of time, usually within seconds. This is of an enormous importance, since the current invention deals with cells which are freely moving within a solution. The latter is to be avoided when screening the cells with DHM, as it can cause disturbed imaging and a problematic analysis. By providing a compartment whereby the cells are essentially immobilized in an instant, the latter is avoided.

In a preferred embodiment, said ratio of the distance between said pair of screening surfaces of said first compartment and said pair of screening surfaces of second compartment comprises between 200:1 and 20:1, preferably 80:1, more preferably 40:1. The latter are optimized for the screening of various types of cell samples by DHM and for acquiring optimal cell densities in the compartments of the sample vial. The exact chosen ratio of the distances within these margins will entirely depend on the nature of the cell sample, the cells present in said cell sample which are to be analysed and the purpose of the analysis. For each of these requirements, an optimal ratio is determined.

In a more preferred embodiment, said the ratio of the surface area of a screening surface of the first compartment and a screening surface of the second compartment comprises between 1:1000 and 50:1, preferably between 1:100 and 10:1, more preferably 1:10, most preferably 1:3. The latter ratios are equally optimized for acquiring optimal cell densities in the compartments of the vial and for a representative scanning by DHM. Again, the exact chosen ratio will depend on the nature of the cell sample.

In a preferred embodiment, said vial comprises two compartments. In a preferred embodiment, said compartments of the vial form respectively a hollow platform as the base of said vial, and a column, preferably vertically placed on said platform.

Said base of vial may comprise any chosen outline, preferably a round, ellipse, rectangular or square outline. Said platform may be cylindrical, cuboid, conical, parallelepiped, or frustroconical. Said column of the vial may be cylindrical, conical, frustro-conical, parallelepiped, or a cuboid.

In one embodiment, said vial comprises at the base of said first compartment, preferably at the centre of said base, a raised area. Said raised area enhances the flow of the cells from the first to the second compartment, hence ensuring an optimal, high cell density in the latter. Especially for cell sample whereby the analysis with said DHM requires a high cell density or a high number of cells, the latter has been proven to be beneficial. Said raised area may be conical, frustro-conical or hemispherical. Cells may migrate from the first to the second compartment under the influence of gravity alone or a vial comprising a cell sample may be rotated in order to help the cells migrating from the first to the second compartment. Therefore, in a preferred embodiment, the vial is easily rotatable around at least one axis. In a more preferred embodiment, the vial comprises at least one axis of rotational symmetry around which the vial can be easily rotated. In a preferred embodiment, said raised area has a shape which is capable of magnifying the image of objects located in said first compartment. In a more preferred embodiment, said raised area comprises a lens-shaped form. Said raised area has an inner surface which preferably bulges inward in the first compartment, and preferably comprises a form whose width near the base of said first compartment is wider than its width further away from said base. More preferably, said raised area comprises an outer surface which is flat, which bulges inward into said first compartment, and/or bulges outward from said compartment, said outer surface preferably comprising a shape suitable for magnifying the image of objects located in said first compartment. In an even more preferred embodiment, said first compartment comprises a liquid medium with a pre-determined medium refraction index and said lens-shaped form comprises at least one curved surface capable of magnifying the image of objects located in said first compartment with a magnification factor depending on said medium refraction index and said curved surface, whereby preferably said magnification factor is pre-fixed and said medium refraction index and/or said cured surface are adapted to result in said pre-fixed magnification factor. In a another embodiment, said second compartment has a stepwise upper surface area, whereby said smallest distance between the two screening surfaces of the second compartment lie at the outer rim of said compartment. This configuration allows obtaining the perfect amount of cells per field of view.

Preferably, said screening surfaces comprise an optically transparent material, whereby said optically transparent material is to be understood as being transparent to light with wavelengths equal to or in the range of the wavelengths of the illumination means of said DHM. Such material can be, but is not limited to glass, plastic, polycarbonate, certain polymers such as polymethylmethacrylaat (PMMA), polystyrene crystals, polycrystalline materials. It should be clear to an artisan skilled in the art that the latter are mere examples, and that other possibilities are readily known. Optionally said material is further treated by for instance a positively charged surface coating such as poly-L-lysine, or by exposing the surface to a plasma treatment, or treated with anti-reflective substances. Preferably, said vial is obtained by extrusion or co-moulding.

In another, preferred embodiment, said sample comprises supporting means at said base of vial. Said supporting means support vial when placed on a surface and prevent said screening surfaces of vial from coming into contact with said surface. The latter prevents said screening surfaces from being scratched or stained by the surface which can cause aberrant or divergent scanning from deviation of the beams of the DHM. Said supporting means may comprise, but are not limited to an upstanding rim at the circumference of the base of said vial or supporting feet at distinct positions of said circumference. Said supporting means may be produced of any material known to artisan skilled in the art, such as plastic, glass or rubber.

In another embodiment, said second compartment can comprise means for evacuating air bubbles. Air bubbles are to be avoided during screening, as the later can cause aberrant analysis. For an adequate and reliable analysis, said second vial should be filled entirely with fluid sample. In one embodiment, said means for discharging air bubbles can comprise grooves, provided at said bottom of said second compartment. Said grooves aid to evacuate any air bubbles present in said second compartment, preferably in the direction of the first compartment and/or the outer environment.

In a preferred embodiment, said vial comprises an opening, preferably said opening is located at the first compartment, in a most preferred embodiment said first compartment being the column. In a preferred embodiment, said opening is capable of engaging with a lid in order to make said vial liquid-tight. In the current invention, the term 'liquid-tight' is to be understood as not allowing any passage or spillage of sample fluid from the inner side of the sample to the outer environment. Said lid preferably comprises a snap-on cap, a friction-fit or a threaded screw-cap. In a more preferred embodiment, said lid comprises an optically transparent material, whereby said material is only optically transparent for light with wave lengths equal to these from the illumination means of DHM and partially or not optically transparent for light with other wavelengths. The latter allows transmission of said illumination beam of DHM and illumination of said sample inside liquid-tight vial. In one embodiment, said lid is entirely produced of an optically transparent material. In another embodiment, said lid is only partially produced from an optically transparent material. In yet another embodiment, said only one specific side or section, such as for instance a window, of said lid is produced from an optically transparent material.

In a preferred embodiment, said opening of first compartment provides for an entrance for receiving a cell collecting device. Said cell collecting device is used for collecting a cell sample from an organism, preferably a human, or for transferring a part of a cell sample stored in a first vial, to a sample vial of the current invention. The cell collecting device may comprise a brush, a spatula, a cotton swab, a needle, a scraper, a pipette or a Pasteur pipette. Preferably, said cell collection device comprises means for collecting a sample, such as a brush, a spatula or a cotton ball, engaged to a longitudinal handle. More preferably, said means for collecting cells is attachable to said longitudinal handle by a snap-release joint as described in EP 2 263 552. The latter allows said means for collecting cells to disengage after collecting the cells from the handle with a simple exertion of pressure. In an embodiment of the invention the means for collecting cells are positioned against a surface inside a sample vial, preferably one of the walls of the first compartment of said vial. This has for effect that the cell collection device can be transferred to a fixation fluid, prior to the disconnection of the sampling head from the longitudinal handle.

By allowing the collected cells ample to be transferred directly from the origin or site of sampling to the sample vial, the transfer of sampled cells is maximized; ease of handling enlarged and the risk of losing cells is reduced.

In a preferred embodiment, said vial comprises means for aiding the disengagement of means for collecting cells from said cell collection device. Preferably, said means for aiding the disengagement are provided to the wall of a compartment, preferably said compartment is the first compartment. Said means for aiding the disengagement may comprise one or more wall protrusions such as for instance pins, and/or one or more wall indentations.

In a preferred embodiment, said fluid connection between said compartments prevents said cell collecting device, more specifically said means for collecting cells, from entering the second compartment of said vial.

In a more preferred embodiment, said vial comprises a sub-compartment for receiving means for collecting cells. Said sub-compartment, is preferably present in the first compartment of said sample vial. The sub-compartment is specifically designed to receive means for collecting cells and retaining said means therein. This prevents said means from freely floating in the vial, thereby possibly obstructing the illumination beams of the DHM when screening through the pair of screening surfaces, hence causing distortion in the analysis. Preferably, said sub-compartment encompasses said means for aiding the disengagement of means for collecting cells.

Said sub-compartment is in liquid connection with the other compartments of said vial. Preferably, said liquid connection is provided by an opening, connecting said sub-compartment with other compartments, or more preferably by a filter membrane, delineating one or more sides of said sub-compartments. Preferably, said filter membrane is designed to ensure passage of both liquid and cells, simultaneously preventing passage of cell debris, tissue clumps and/or mucus. Preferably, said filter membrane comprises a mesh which pore size is optimized for the latter.

Preferably, when said sample vial is provided with a sub-compartment for receiving means for collecting cells and with a lid for making vial liquid-tight, said lid is only partially produced of an optically transparent material, preferably at one side or one section of said lid, such as a window. Preferably, said side or section produced of an optically transparent material is located opposite from said sub-sub-compartment for receiving means for collecting cells, when said lid is engaged in a liquid-tight manner to said vial.

Alternatively, in another preferred embodiment, said vial is internally provided with a filter membrane, whereby said filter membrane is located at either the first compartment or at the fluid connection of said first and second compartment. Preferably, said filter membrane will span an entire section of said first compartment or section determining fluid connection between said first and second compartment. Said filter membrane ensure passage of cells and liquid, but prevent passage of mucus, cell debris and tissue particles, which are undesirable during screening by DHM.

In another preferred embodiment, said sample vial comprises identifying indicia, said indicia may be fixed indicia and/or programmable indicia. Said indicia can correlate to type of sample, information on the origin of sample such as patient identity, general patient ID info (e.g. age, gender, residential area, . . . ), sample information (e.g. place and time when the sample was taken), owner ID info (e.g. the name of the user/institution from which the info comes from), DHM-ID info (e.g. a serial number of the DHM with which the DHM-obtained object properties are measured or observed), etc. or any combination thereof. Said identifying indicia are preferably machine-readable. In one embodiment, said indicia comprise a bar code label, which corresponds to and uniquely identifies the vial and the sample contained therein. In a most preferred embodiment, said indicia comprise an RFID tag. The indicia are read by identifying means, such as a laser scanner bar code reader in the case of the indicia being a bar code, or an RFID reader when indicia being an RFID tag. Additionally, information related to the date and time of the obtained holographic information can be added, in addition to the initial sample indicia. Optionally, the name or other identifier of the cytological laboratory analysing the sample with the system may be linked to the identification information as well.

Preferably, said all of the above-mentioned data is obtained by screening the sample in the first and/or second compartment of the vial via a scanning-pattern. Said scanning pattern may comprise a random line-pattern, a non-periodically line-pattern, a periodically line-pattern, a continue or discontinue pattern, a zigzag pattern, a line-pattern with phase and amplitude etc. Said screening the sample via a line-pattern ensures that the DHM will scan only unique sections of said sample, hence preventing that one section is screened multiple times. The latter ensures that significantly reliable and adequate information is obtained from said cell sample. Preferably, when a sufficient amount of cells is screened by said DHM, hence gathering enough information for a reliable analysis, said screening will be automatically stopped.

Aspects of the invention further include systems for use in practicing the subject methods. Systems of interest include a Digital Holographic Microscope configured to assay a liquid sample for both morphological and biomarker data, e.g., as described above. Said system comprises a digital holographic microscope and at least one sample vial according to the current invention, characterized in that system comprises means for screening said sample via a scanning pattern. Preferably, said means may comprise a movable platform or sample vial holder, whereby said platform or holder will move said sample vial during analysis of said sample. Preferably, said movement involves a rotational movement. In another embodiment, said means may comprise a movable lens, movable illumination means of said DHM or means that can alter the pathway of said illumination means such as for instance a mirror.

Accordingly, aspects of the invention further include systems, e.g., computer based systems, which are configured to predict the presence of a CIN lesion in a subject, e.g., as described above. A "computer-based system" refers to the hardware means, software means, and data storage means used to analyse the information of the present invention, e.g. the threshold database and used queries according to the current invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Embodiments of the subject systems include the following components: (a) a communications module for facilitating information transfer between the system and one or more users, e.g., via a user computer, as described below; and (b) a processing module for performing one or more tasks involved in the quantitative analysis methods of the invention.

In certain embodiments, a computer program product is described comprising a computer usable medium having control logic (computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

The subject methods and systems find use in a variety of different applications where detection prediction of the presence of (pre)cancerous cells in a subject is desired. Such applications include both research and diagnostic applications, e.g., applications where a subject is diagnosed with respect to the presence of or propensity to develop cervical cancer, e.g., as described above. The clinical utility of the methods and systems described herein provide powerful tools to detect and screen for the presence of cancerous cells and cancer development, both early and late stages, thus allowing therapeutic intervention to prevent disease progression as well as a chance to provide early treatment.

In addition, in an embodiment, the subject methods and systems finds use in the prognosis or risk assessment of an HPV-related disease or condition, for monitoring of the evolution of an HPV-related disease or condition, and for monitoring the efficiency of an anti-HPV drug or treatment, such as e.g., an anti-HPV vaccine or an anti-HPV vaccine candidate.

In yet another aspect, the present invention provides kits for practicing the subject methods, e.g., as described above. The subject kits may include a separate set of labelled biomarker probes en liquid medium, e.g., as described above, to be combined prior to sample solubilisation. In another embodiment, said kit comprises the liquid medium already supplemented with biomarker probes. Said kit may furthermore comprise a sample vial according to the current invention, empty or pre-filled with the liquid medium (either with or without biomarker probes) according to the current invention. Kits may further include sample obtainment devices, e.g., cervical brooms, as described above. The above components may be present in separate containers or one or more components may be combined into a single container, e.g., a glass or plastic vial.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

Figure 1B:
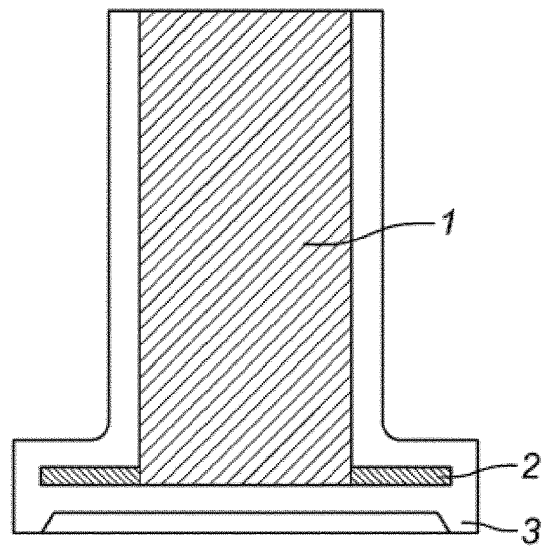
Figure 6A:
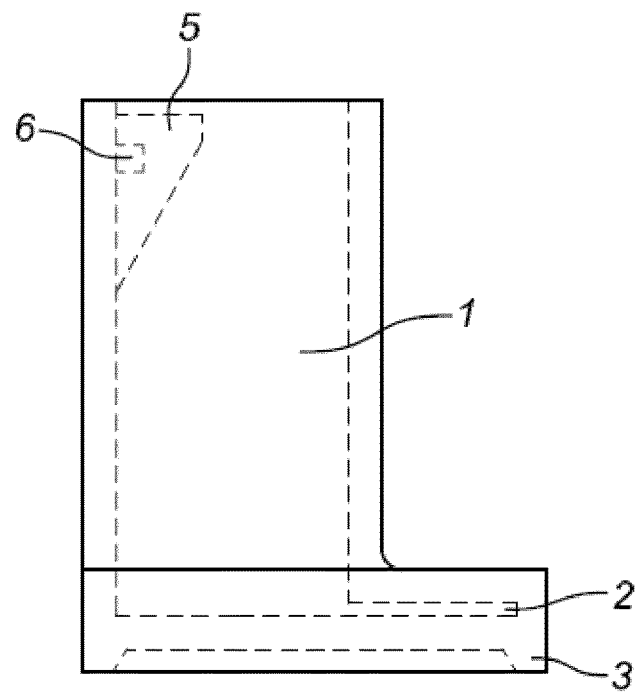
Figure 6B:
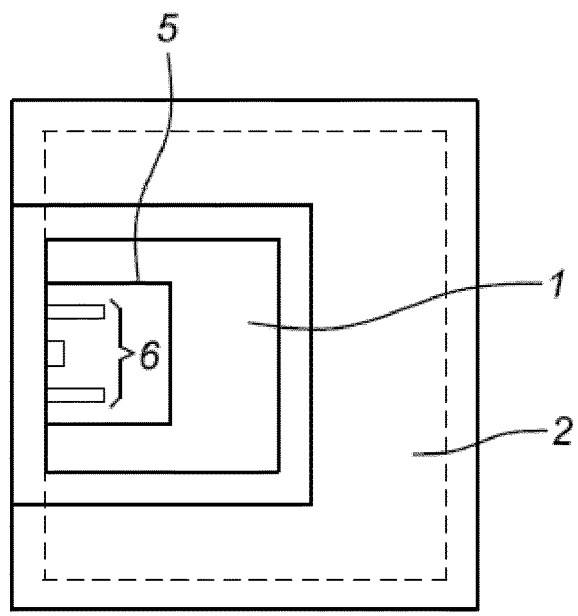
Figure 7A:
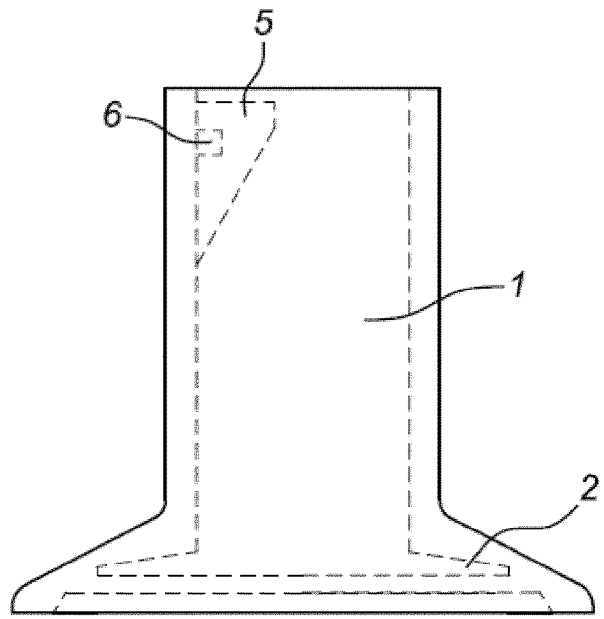
Figure 7B:
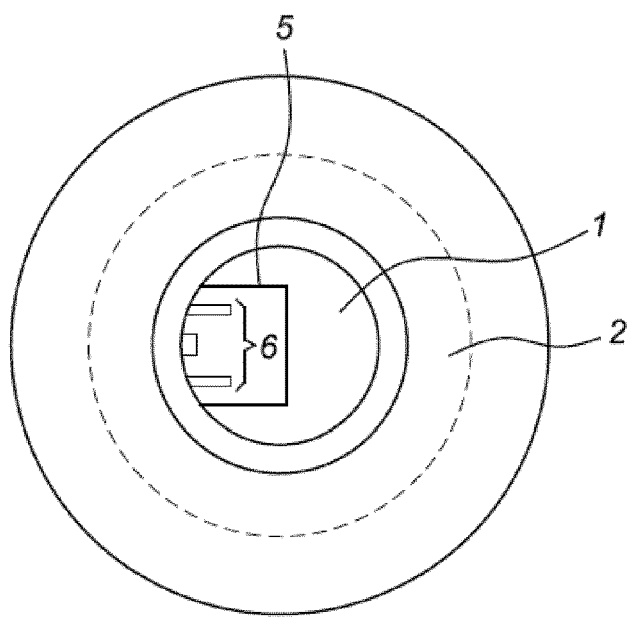
Figure 9A:
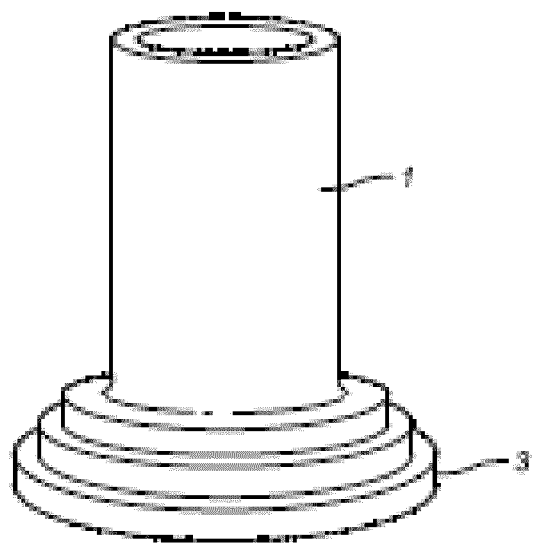
Figure 9B:
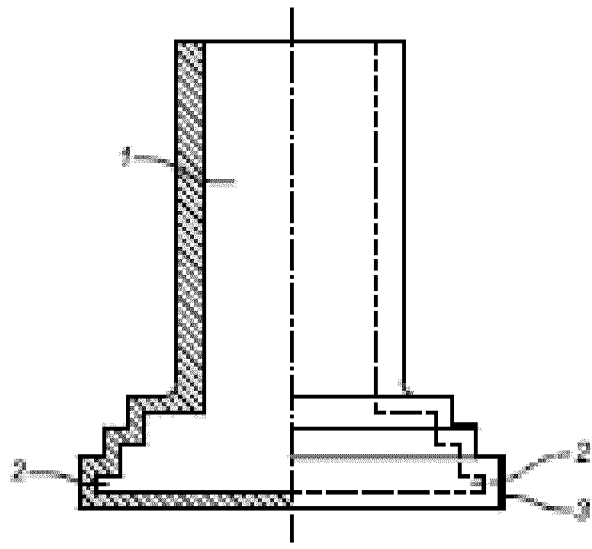

FIGS. 1 to 7 and 9 depict preferred embodiments of the sample vial according to the current invention. Said sample vial comprises a first (1) and second (2) compartment, whereby said first (1) and second (2) compartment are in liquid connection with one other and whereby each said compartment comprises a pair of screening surfaces. The shading pattern in FIG. 1b defines further the meaning of said first (1) and second compartment (2). For instance, said sample vial may be T-shaped, comprised of cylindrical compartments as shown in FIG. 1, or comprised of cuboids (FIG. 5) or comprised of a combination of cylindrical and frustro-conical compartments (as shown in FIG. 7). Alternatively, said vial may be L-shaped, as shown in FIG. 6. FIG. 9 shows an embodiment of the vial with a stairwise formed second compartment.

Figure 2A:
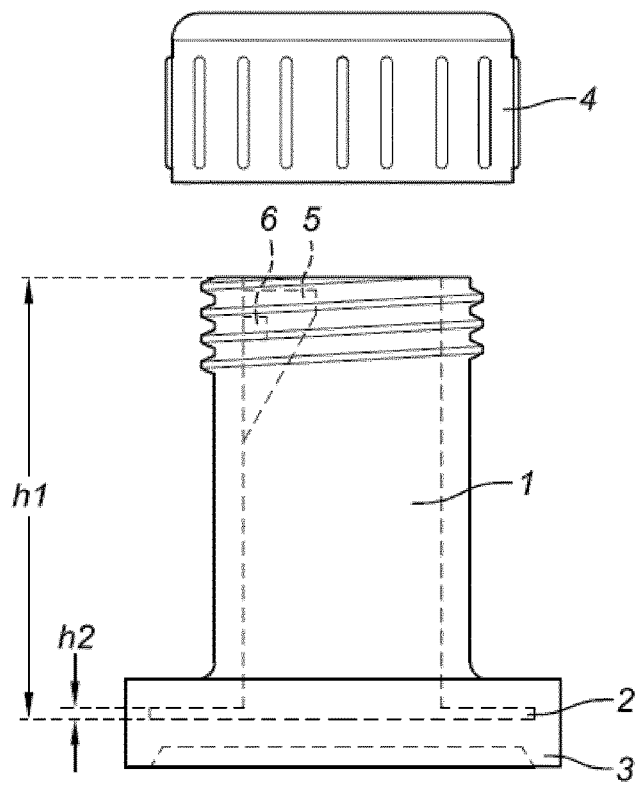
Figure 3:
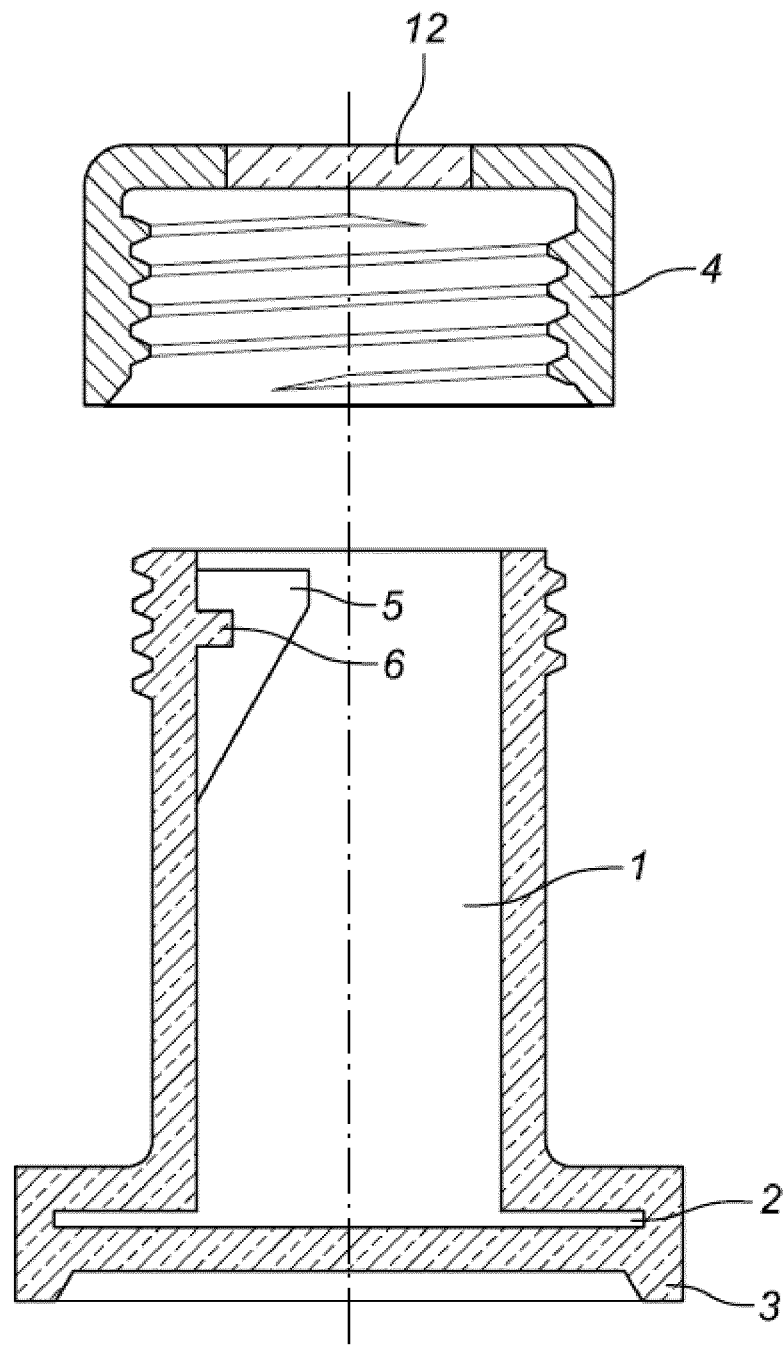

As shown in FIGS. 2a and 3, the vial may be provided with a lid (4), making said vial liquid-tight when said lid is engaged to said vial. Preferably said lid (4) is a screw cap. Said vial may comprise an optically transparent material, whereby said optically transparent material may be restricted to for instance only a section of said lid. The lid (4) of the sample vial as depicted in FIG. 3 comprises a window (12), comprised of optically transparent material. Said window allows screening of the sample by DHM through the lid (4).

The sample vial is preferably foreseen of supporting means (3) at the base of the vial, for providing support when placed on a surface. Said supporting means (3) prevent the screening surfaces at the base of the vial from being scratched and/or stained.

Figure 8A:
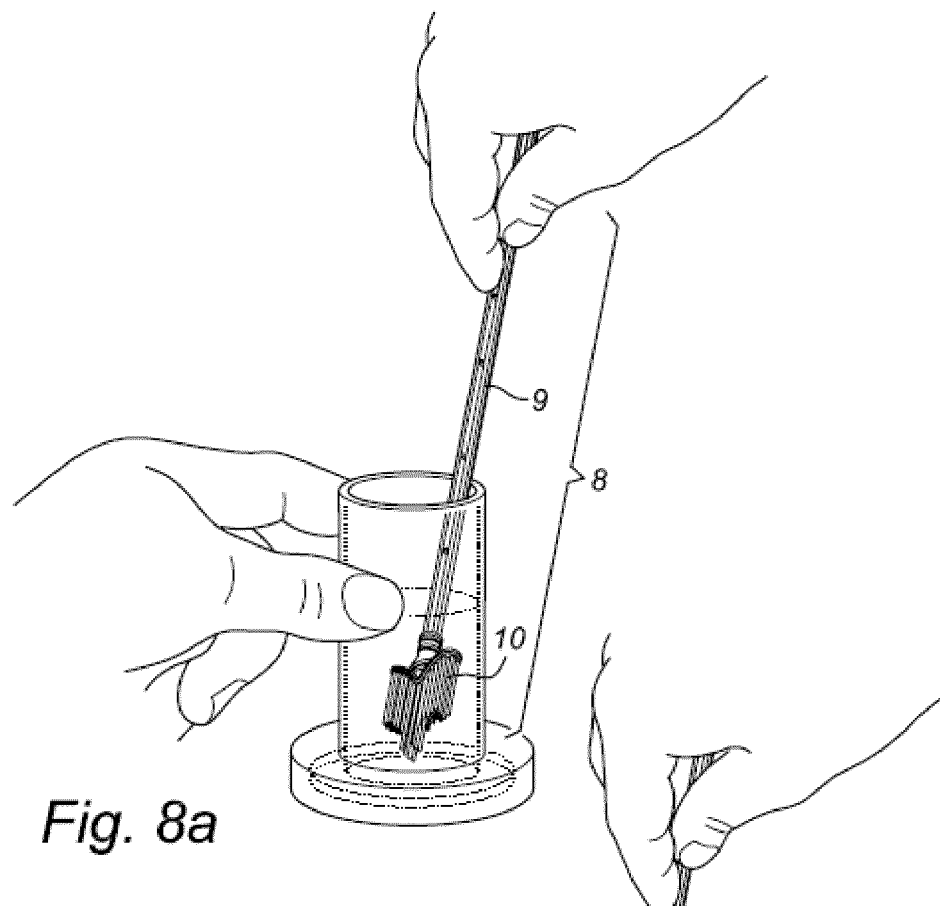
FIG. 8 shows exemplary ways of providing a cell sample collected by a cell collecting device to a sample vial according to an embodiment of the current invention.
Figure 8B:
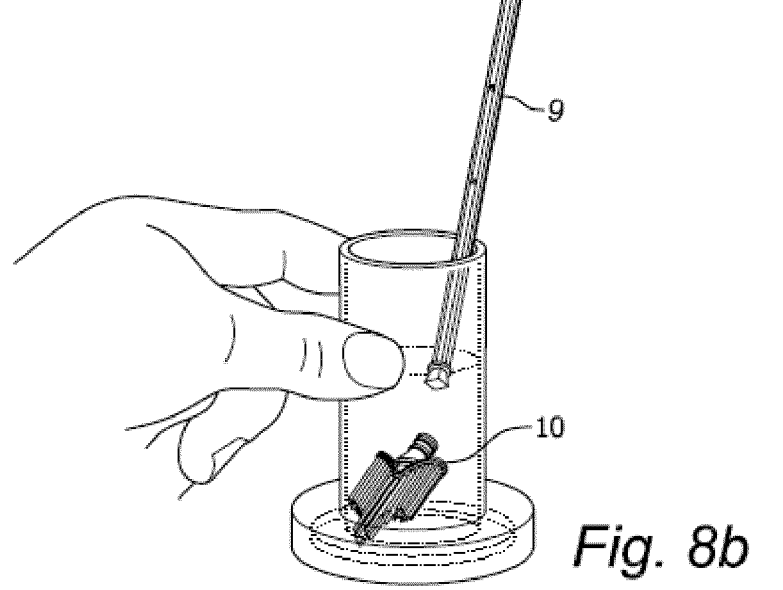
Figure 8C:
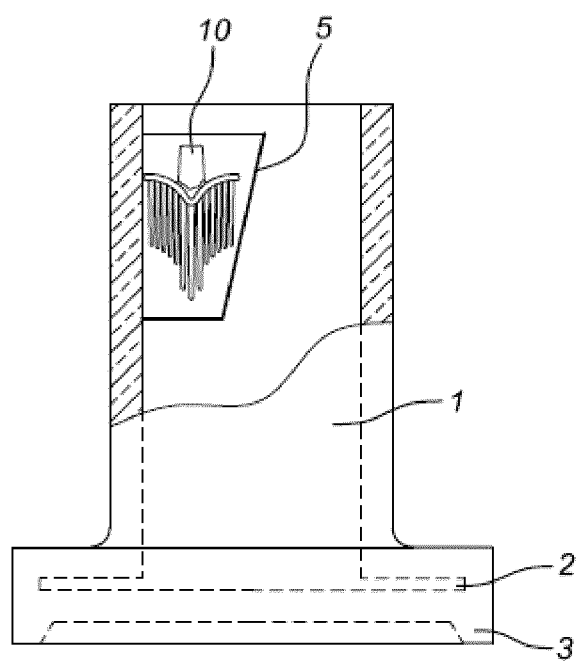

For specific purposes, the vial may be equipped with a sub-compartment (5) and/or means for aiding the disengagement (6) of means for collecting cells (10) from a cell collection device (8) and the handle (9) of the cell collection device (8). The means for aiding the disengagement may be, as shown in FIGS. 2 to 7, protrusions (6) extending from the wall of the first compartment (1). In the current example, these protrusions will help a practitioner with the disengagement of a sample brush (10) from a longitudinal handle and is preferably encompassed by a sub-compartment (5). This sub-compartment is designed to receive the sample brush (10) or any other means for collecting cells. As shown in FIG. 8, multiple ways of providing the collected cells from a cell collecting device (8) to the sample vial exist. The cells may be provided by a stirring movement of the device (8) as shown in FIG. 8a. Through the stirring, the collected cells will 'fall' from the brush (10) and disperse in the preservative solution provided in the sample vial. Alternatively, the means for collecting cells (10), in the current example a brush, will be disconnected from the handle (9), leaving the brush at the bottom of the first compartment of the vial (see FIG. 8b). The fluid connection between the first and second compartment will prevent the brush from entering the second compartment. Another option is shown in FIG. 8c, whereby the sample vial is provided in the first compartment with a sub-compartment (5), for receiving and retaining the brush (10), after the latter is released from the handle (9). The sub-compartment (5) and brush (10) remains in fluid connection with the first compartment, allowing the collected cells to migrate from the sub-compartment to the first and second compartment. Preferably, this connection is ensured by a filter membrane delineating the sub-compartment (5) or an opening in said sub-compartment (5).

Figure 4:
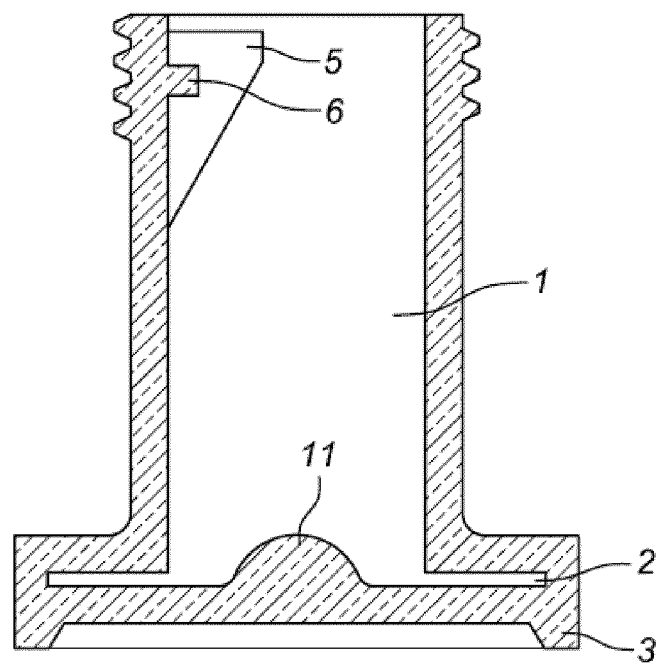
Figure 5A:
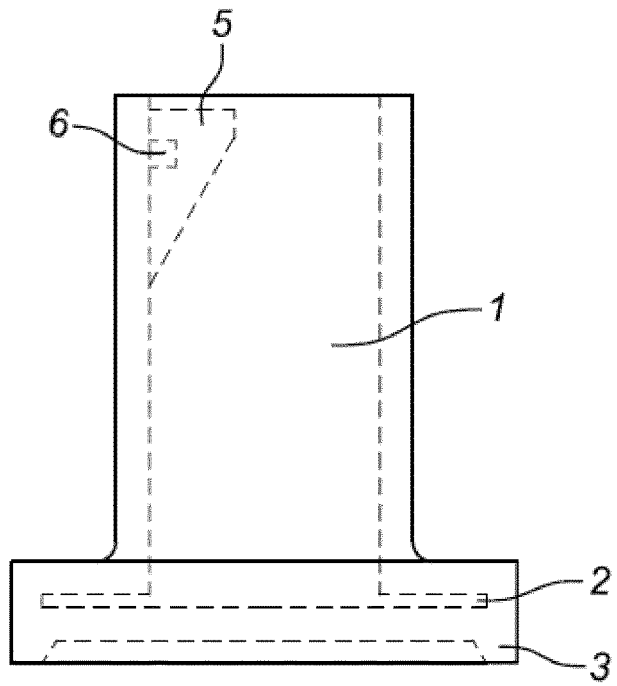
Figure 5B:
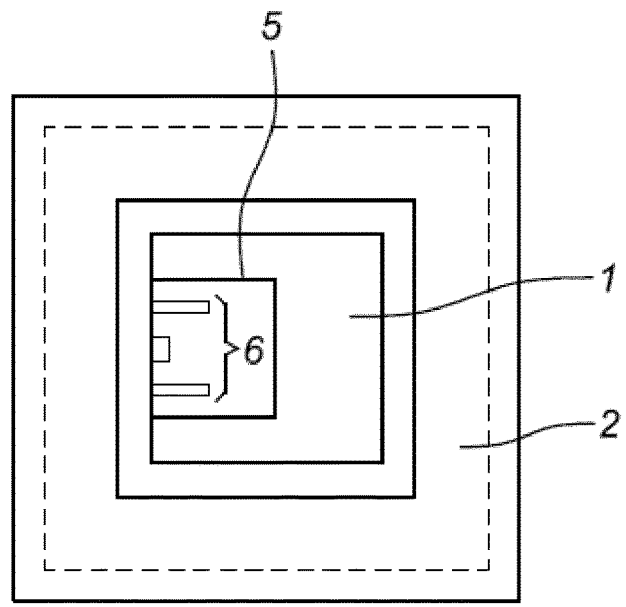

As shown in FIG. 4, the base of the first compartment (1) of the vial may at the inner side be accommodated with a raised area (11). The raised area (11) enhances the flow of the cells from the first to the second compartment, hence ensuring an optimal, high cell density in the latter.

Figure 2B:
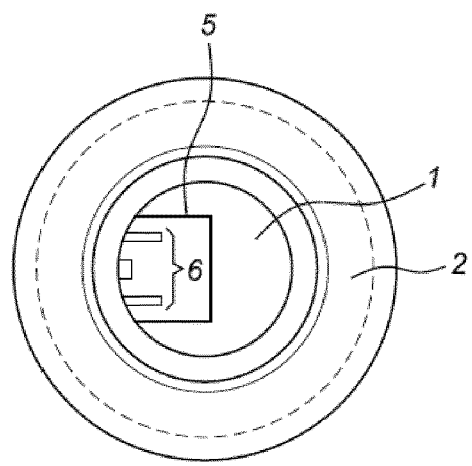

As shown in FIG. 2a, the distance (h2) between the pair of screening surfaces of the second compartment (2) is smaller than the distance (h1) between the pair of screening surfaces of the first compartment (1). This is important as the latter will provide different cell densities in both compartments. Dense cell layers, comprising a few layers or even only one layer of cells will be achieved in the second compartment, whereas lesser dense layers will be achieved in the first compartment (1). For instance, a sample vial as shown in FIG. 1 or FIG. 2, suitable for the screening of a cervical cell sample by DHM, may comprise the following dimensions:

h1: 42 mm
h2: 1 mm
surface area A1: ±452 mm$^2$
surface area A2: ±1537.34 mm$^2$ Experimental Example 1

Samples of 16 selected patients previously diagnosed by the Thinprep® liquid based cytology confirmed by HPV Abott® assay or histology diagnosis for CIN2/3, were obtained and analyzed by the method of the current invention. Samples were collected by means of a cervical brush and immediately solubilized in a liquid medium of the current invention, comprising a labelled (fluorescent) biomarker against either HPV E6 or E7 protein (samples were divided in two groups of 8 samples, one group received the liquid medium with anti-E6, the other with anti-E 7).

DHM enables a quantitative multifocal phase contrast imaging that has been found suitable for quantitative and qualitative inspection, and for 3-dimensional cell imaging. Both biomarker data and morphological data was obtained.

188 cells were identified and measured in an automated way. Cells were in a first instance analyzed based on the presence of HPV specific proteins. In a second instance, information regarding the Nucleus/Cell Ratio (NCR) and Optical Height Delta (OHD) was extracted from the 3D holographic image. The Optical Height Delta is the difference between Nucleus top height minus Cytoplasm average height. NCR and OHD were separately determined in 2 groups: CIN1 or CIN 2/3 patients.

These results were compared with normal cells either from patients with normal cytology diagnosis either from normal cells within the abnormal smears. Data were imported in the global data sheet and statistical ROC analysis and Area Under de Curve (AUC) were performed.

|  | Negative | Positive | p value ANOVA | AUC (ROC) |
|---|---|---|---|---|
| CIN1 |  |  |  |  |
| n | 66 | 122 |  |  |
| NCR | 0.30 +/− 0.23 | 0.39 +/− 0.17 | 0.002 | 0.71 |
| OHD | 0.22 +/− 0.09 | 0.34 +/− 0.14 | <0.0001 | 0.75 |
| CIN2, 3 |  |  |  |  |
| n | 83 | 105 |  |  |
| NCR | 0.29 +/− 0.21 | 0.41 +/− 0.17 | <0.0001 | 0.76 |
| OHD | 0.23 +/− 0.10 | 0.35 +/− 0.14 | <0.0001 | 0.75 |

Figure 10:
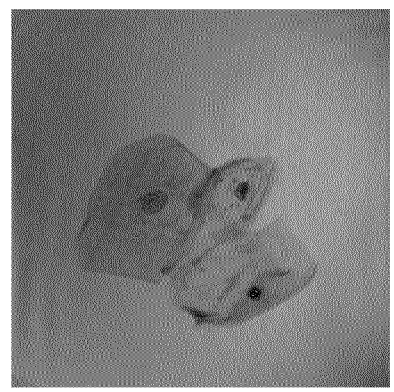
FIG. 10 depicts a three-dimensional image of cells in a cell sample, obtained by DHM.
Figure 10:
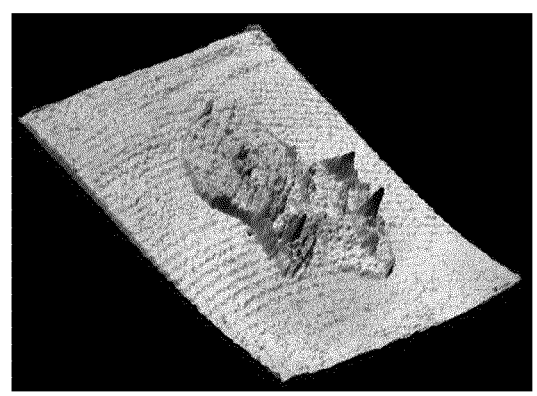
Figure 10:
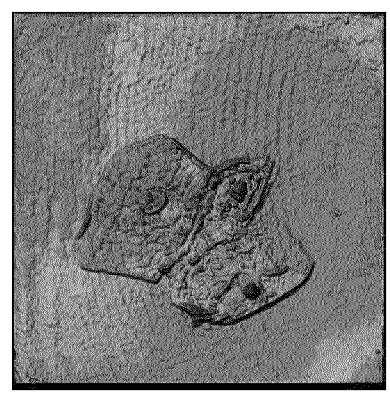
Figure 11:
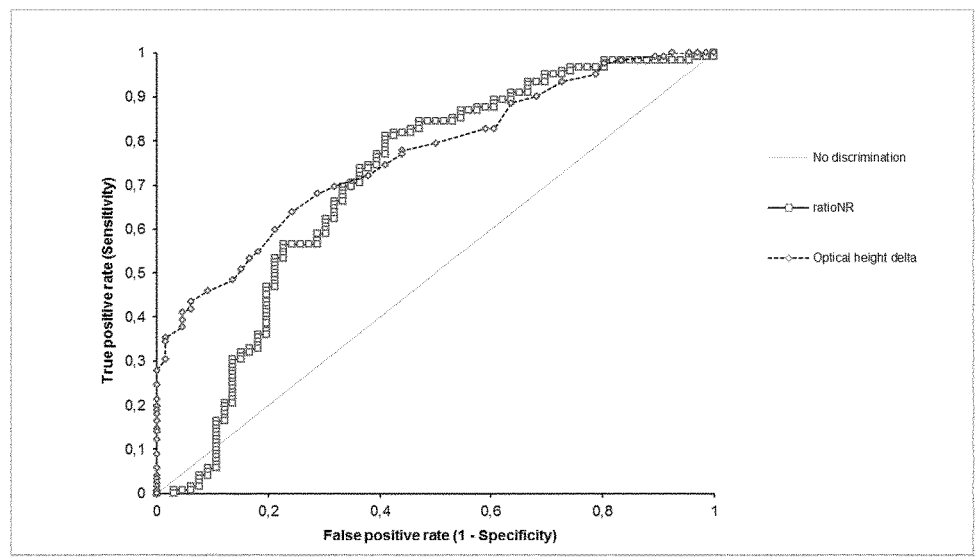
FIG. 11A depicts a graphical overview of results obtained by the method according to the current invention, for cervical cells with diagnostic status equal to or higher than CIN1.
FIG. 11B depicts a graphical overview of results obtained by the method according to the current invention, for cervical cells with diagnostic status equal to or higher than CIN2.
Figure 11:
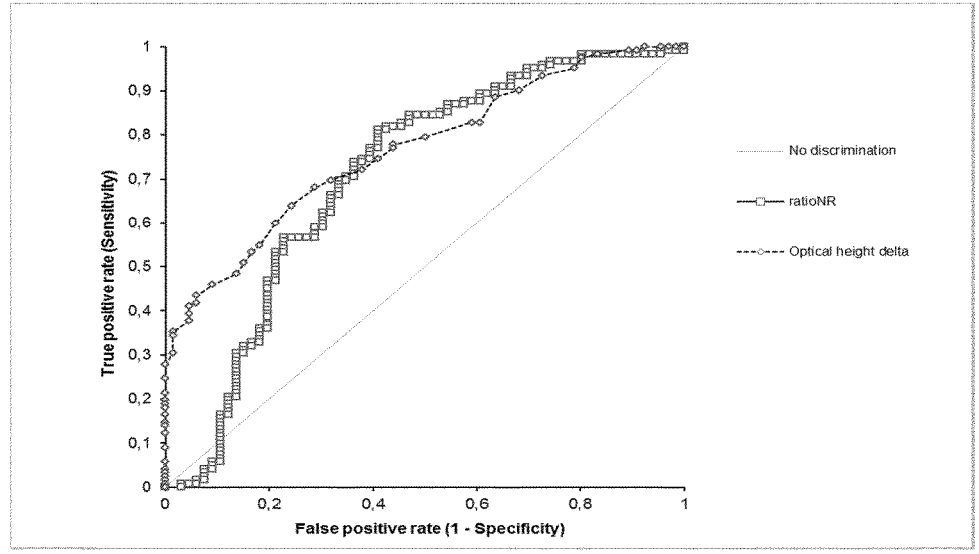

Graphical overview of the obtained results are shown in FIGS. 11A and 11B. Cell population analysis by this objective tool reveals an increased NCR and OHD in the dysplastic cells. A correlation can be observed between the OHD and the diagnosis. This correlation allows the application of an automatic scoring algorithm in a smear in a liquid cell sample without the need for additional expensive preparation to make a cytological diagnosis. FIG. 10 A-C show examples of morphological data obtained from one of the analyzed sample, whereby the morphological data comprise two-dimensional and three-dimensional images from cells present within sample.

Eighty percent of the samples which were predicted to be a CIN 2 or CIN 3 showed positive signal for E6 or E7, while 23% of the CIN1 categorized samples were found positive.

Experimental Example 2

In a similar set-up, cervical samples of 15 patients were obtained and solubilized in a liquid medium of the current invention, comprising a fluorescently labelled bio-marker against p16 (antibody). A linear correlation between cells found to be positive for p16 and predicted cancerous based on the obtained morphological data was shown.

Experimental Example 3

Experiment 1 and 2 were samples from the same patients, this time with biomarkers labelled with gold plated nanoparticles. Comparable results were obtained as in example 1 and 2.

The method of the current invention, using combined morphological and biomarker data (e.g. E6, E7, p16, p16INK4a, Ki-67 or annexin A5 overexpression) on a cell-by-cell basis performed on cells in suspension increased the sensitivity and specificity for detection of (pre)cancerous cells (e.g. a CIN2 an CIN3 lesion to more than 90%, compared to currently known single tests such as PAP smear and HPV DNA.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for obtaining data from a cell sample containing cells from a subject at risk of cancer or pre-cancer, comprising the steps of:
    suspending and preserving the cell sample in a sample vial comprising a liquid medium, said liquid medium comprising a component configured to label cells or epitope(s) on or in said cells; and
    obtaining data from said labelled liquid cell sample by digital holographic microscopy on the suspended cells of the cell sample in the sample vial,
    wherein said data comprises morphological data and biomarker data, said morphological data comprising optical nuclear height, nuclear volume, nuclear volume variability, or any combination thereof.

2. The method according to claim 1, wherein said morphological data and biomarker data are simultaneously obtained.

3. The method according to claim 1, wherein said sample is solubilized immediately after obtainment.

4. The method according to claim 1, wherein said morphological data further comprises cell nucleus diameter, chromatin texture, cell size, percent nucleation, cell form, cell quantity, nuclear size, nuclear size variability, chromatin texture, or any combination thereof.

5. The method according to claim 1, wherein said liquid cell sample comprises cervical cells.

6. The method according to claim 1, wherein said component configured to label cells or epitopes on or in said cells comprises a labelled biomarker probe for obtaining biomarker data.

7. The method according to claim 6, wherein said biomarker probe is directed against at least one of the markers selected from the group consisting of p14Arf, p15INK4b, p16INK4a, p18INKc, p19INK4d, p21WAF1/CIP1, p27Kip1, Ki-67, Annexin A5, HPV viral proteins E1, E2, E3, E4, E5, E6, E7, L1, L2; and any combinations thereof.

8. The method according to claim 1, wherein said obtained morphological data is compared to and correlated with a reference database.

9. The method according to claim 8, wherein said obtained morphological data is stored in said reference database.

10. The method according to claim 6, wherein said biomarker data is obtained by omitting background originating from labeled biomarker probe which is unbound.

11. The method according to claim 8, wherein said reference database is a threshold database comprising a set of thresholds related to known cellular parameters in order to classify said cells with respect to their health status.

* * * * *

UNITED STATES PATENT AND TRADEMARK OFFICE
CERTIFICATE OF CORRECTION

PATENT NO. : 10,060,905 B2
APPLICATION NO. : 14/359553
DATED : August 28, 2018
INVENTOR(S) : Olivier Magniette It is certified that error appears in the above-identified patent and that said Letters Patent is hereby corrected as shown below:

In Column 2, Line 17, change "Caviation" to --Cavitation--.

In Column 8, Line 48, change "Gluoosid," to --Glucoside,--.

In Column 8, Line 54, change "RhCI3," to --RhCl3,--.

In Column 9, Lines 50-53, change "or less, 10-8 M or less, 10-9 M or less, 10-19 M or less, 10-11M or less, 10-12 M or complex is characterized by a Kd (dissociation constant) of 10-6 M or less, 10-7 M less, 10-13 M or less, 10-14 M or less, including" to --complex is characterized by a Kd (dissociation constant) of 10-6 M or less, 10-7 M or less, 10-8 M or less, 10-9 M or less, 10-10 M or less, 10-11 M or less, 10-12 M or 30 less, 10-13 M or less, 10-14 M or less, including--.

In Column 10, Line 37, change "2,2'disulfonic" to --2,2'-disulfonic--.

In Column 10, Line 38, change "acrindine" to --acridine--.

In Column 10, Lines 40-41, change "vinylsulfonyl)" to --(vinylsulfonyl)--.

In Column 10, Line 41, change "5disulfonate" to --5-disulfonate--.

In Column 10, Line 45, change "trifluoromethylcouluarin (Coumaran" to --trifluoromethylcoumarin (Coumarin--.

In Column 12, Line 8, change "111A" to --IIIA--.

In Column 12, Line 8, change "(niphedipine" to --(nifedipine--.

In Column 12, Line 9, change "nonpolyposistype" to --nonpolyposis type--.

In Column 12, Line 31, change "(mephenyloin" to --(mephenytoin--.

Signed and Sealed this
Eleventh Day of December, 2018

Andrei Iancu
*Director of the United States Patent and Trademark Office*

CERTIFICATE OF CORRECTION (continued)
U.S. Pat. No. 10,060,905 B2

In Column 12, Line 38, change "MMPI" to --MMP1--.

In Column 12, Line 39, change "1L2" to --IL2--.

In Column 12, Line 48, change "Nacetyltransferase)," to --N-acetyltransferase),--.

In Column 12, Line 55, change "amyloidprecursor)," to --amyloid precursor),--.

In Column 12, Lines 60-61, change "zetapolypeptide," to --zeta polypeptide,--.

In Column 12, Line 66, change "AP0A1" to --APOA1--.

In Column 13, Line 26, change "inhibitorof" to --inhibitor of--.

In Column 13, Line 36, change "E2F1E2F" to --E2F1 E2F--.

In Column 13, Lines 47-48, change "receptorantagonist," to --receptor antagonist,--.

In Column 13, Line 61, change "antagonistlkiller" to --antagonist/killer--.

In Column 14, Line 7, change "apoptosls" to --apoptosis--.

In Column 14, Line 44, change "11A," to --IIA,--.

In Column 14, Line 51, change "relatedcysteine" to --related cysteine--.

In Column 15, Line 5, change "G/Hsynthase" to --G/H synthase--.

In Column 15, Lines 23-24, change "acyftransferase," to --acyltransferase,--.

In Column 15, Lines 24-25, change "topolsomerase" to --topoisomerase--.

In Column 15, Line 59, change "EWSR1Ewing" to --EWSR1 Ewing--.

In Columns 16-17, Line 67 of Column 16 and Line one of Column 17, change "methoxyactridine." to --methoxyacridine.--.

In Column 17, Line 47, change "clandular" to --glandular--.

In Column 30, Line 37, change "en" to --in--.

In Column 32, Line 29, change "E 7)." to --E7).--.